United States Patent
Otsuki et al.

(10) Patent No.: US 8,476,035 B2
(45) Date of Patent: Jul. 2, 2013

(54) AGENT THAT MODULATES PHYSIOLOGICAL CONDITION OF PESTS, INVOLVED IN INSECT CHOLINE ACETYLTRANSFERASE ACTIVITY

(75) Inventors: Junko Otsuki, Toyonaka (JP); Marc Van De Craen, Aalter (BE); Annelies Roobrouck, Mater (BE); Guy Nys, Aalter (BE); Bert Demey, Ingelmunster (BE)

(73) Assignee: Sumitomo Chemical Company, Limited, Tokyo (JP)

( * ) Notice: Subject to any disclaimer, the term of this patent is extended or adjusted under 35 U.S.C. 154(b) by 218 days.

(21) Appl. No.: 12/743,866

(22) PCT Filed: Nov. 21, 2008

(86) PCT No.: PCT/JP2008/071748
§ 371 (c)(1),
(2), (4) Date: Oct. 8, 2010

(87) PCT Pub. No.: WO2009/066800
PCT Pub. Date: May 28, 2009

(65) Prior Publication Data
US 2011/0028423 A1    Feb. 3, 2011

(30) Foreign Application Priority Data
Nov. 22, 2007   (JP) .................................. 2007-302699

(51) Int. Cl.
*C12Q 1/48*   (2006.01)

(52) U.S. Cl.
USPC .......................................................... 435/15

(58) Field of Classification Search
USPC .......................................................... 435/15
See application file for complete search history.

(56) References Cited

PUBLICATIONS

Baillie, et al., "Inhibitors if Choline Acetyltransferase as Potential Insecticides," Pestic. Sci., 1975, pp. 645-653, vol. 6, XP002519116.
Banerjee, et al., "Effect of Pyrethrum on CNS and Haemolymph Monovalent ($Na^+$, $K^+$) Cations and Also on the Level on CNS Acetylcholine and Activities of Esterase and Choline Acetyltransferase in the Insect *Schizodactylus monstrosus* Drury," Neurochem. Int., 1987, pp. 135-141, vol. 10, No. 2, XP-002519117.
Sastry, et al., "Relationships Between Chemical Structure and Inhibition of Choline Acetyltransferase by 2-(α-Naphthoyl)Ethyltrimethylammonium and Related Compounds[1,2]," Pharmacological Research Communications, 1988, pp. 751-771, vol. 20, No. 9, XP009113399.
Alfonso, et al., Cloning and Characterization of the Choline Acetyltransferase Structural Gene (cha-1) from *C. elegans*, The Journal of Neuroscience, Apr. 1994, pp. 2290-2300, vol. 14, No. 4, XP002519118.

*Primary Examiner* — Maryam Monshipouri
(74) *Attorney, Agent, or Firm* — Sughrue Mion, PLLC

(57) ABSTRACT

The present invention provides an agent that modulates physiological condition of pests, wherein the agent has an ability to modulate the activity of an insect choline acetyltransferase; a method for assaying pesticidal activity of a test substance, which comprises measuring the activity of a choline acetyltransferase in a reaction system in which the choline acetyltransferase contacts with a test substance, and the like.

9 Claims, No Drawings

AGENT THAT MODULATES PHYSIOLOGICAL CONDITION OF PESTS, INVOLVED IN INSECT CHOLINE ACETYLTRANSFERASE ACTIVITY

This application is a 371 of PCT/JP2008/071748, filed Nov. 21, 2008, which claims priority to Japanese application 2007-302699, filed Nov. 22, 2007.

SEQUENCE LISTING

The instant application contains a Sequence Listing which has been submitted via EFS-Web and is hereby incorporated by reference in its entirety. Said ASCII copy, created on May 19, 2010, is named Q118912.txt and is 13,556 bytes in size.

TECHNICAL FIELD

The present invention relates to an agent that modulates physiological condition of pests, involved in insect choline acetyltransferase activity, and the like.

BACKGROUND ART

Choline acetyltransferase (acetyl CoA:choline O-acetyltransferase, EC 2.3.1.6; synonym: Choline acetylase, Choline O-acetyltransferase; ChAT) is the enzyme responsible for catalyzing the biosynthesis of the neurotransmitter acetylcholine from its precursors, acetyl-coenzyme A (acetyl-CoA) and choline. Acetylcholine was the first neurotransmitter to be reported and plays a pivotal role in such fundamental brain processes as learning, memory and sleep. Acetylcholine functions in the cholinergic neurons of the peripheral and central nervous systems. In the peripheral nervous system acetylcholine stimulates muscle contraction through the neuron-muscular junction and in the central nervous system acetylcholine facilitates learning and short-term memory formation.

There have been reports on choline acetyltransferase from invertebrates including insects as follows. The *C. elegans* choline acetyl transferase is enriched in synaptic regions of cholinergic neurons (Duerr et al., Midwest Worm Meeting abstract 39). A loss-of-function mutation in *C. elegans* choline acetyltransferase gene leads to growth arrest at L1 larval stages and death (Yook and Jorgensen, West Coast Worm Meeting abstract 260). A severe reduction-of-function mutation in *C. elegans* choline acetyltransferase gene leads to slow growth, small body size and an irregular defecation cycle (Rand and Russell, Genetics, 106(2):227-248, 1984). The mutation leads to resistance to acetylcholine esterase inhibitors such as aldicarb or trichlorfon presumably due to undersynthesis of acetylcholine (Rand and Russell, Genetics, 106 (2):227-248, 1984).

Choline acetyltransferase is widely distributed in the central nervous system of *Drosophila melanogaster* throughout all developmental stages (Gorczyca and Hall, J. Neurosci., 7(5): 1361-1369, 1987). Recessive non-conditional loss-of-function mutants for the *Drosophila melanogaster* choline acetyltransferase gene die at the late embryonic stage (Greenspan, J. Comp. Physiol., 137(1):83-92, 1980). Temperature sensitive reduction-of-function mutants for *Drosophila melanogaster* choline acetyltransferase become paralysed after incubation at a restrictive temperature (Kitamoto et al., J. Neurobiol., 42(2):161-171, 2000). Using temperature-sensitive loss-of-function mutation at the *D. melanogaster* choline acetyltransferase locus, it has been shown that normal acethylcholine metabolism is not required for the initial formation of the nervous system but is required for the subsequent maintenance of its structural integrity and function (Chase and Kankel, Dev. Biol., 125(2):361-380, 1988).

Discovery of agricultural chemicals has traditionally been based on a random screening process, often directly testing the effects of specific chemicals on whole organisms, such as insects, fungi and/or plants, and determining biological activity. Once chemical compounds with the appropriate biological activity are discovered, more intense research is required to specifically determine the mode of action or site of action of these compounds at the molecular level, in order to predict safety and environmental load of these compounds.

DISCLOSURE OF INVENTION

This invention describes a more target-based approach of screening agricultural chemicals, whereby compounds are screened against a specific target that has been identified as biologically and/or physiologically relevant with intent of chemically interfering with the target site to control pest organisms.

Specifically, this invention describes that an agent that modulates physiological condition of pests and having an ability to modulate the activity of an insect choline acetyltransferase is useful to control pests.

That is, the present invention provides:

1. An agent that modulates physiological condition of pests, wherein said agent has an ability to modulate the activity of an insect choline acetyltransferase;
2. An agent according to item 1, wherein said choline acetyltransferase is a cotton aphid choline acetyltransferase;
3. An agent according to item 1, wherein said agent is a pesticidal agent;
4. An agent according to item 1, wherein said ability to modulate the activity of an insect choline acetyltransferase is an ability to inhibit a reaction of the insect choline acetyltransferase with acetyl-CoA and choline;
5. A pesticidal agent which comprises a substance that has an ability to modulate the activity of an insect choline acetyltransferase or an agriculturally acceptable salt of the substance as an active ingredient;
6. A pesticidal agent according to item 5, wherein said substance has an ability to inhibit a reaction of the insect choline acetyltransferase with acetyl-CoA and choline;
7. A pesticidal agent according to item 6, wherein said substance has an ability to inhibit the reaction of the insect choline acetyltransferase with acetyl-CoA and choline in a cell-free system, wherein in the presence of said substance of 10 micro M or more the activity of said choline acetyltransferase is lower than that in the absence of said substance;
8. A pesticidal agent according to item 6, wherein said substance has an ability to inhibit a reaction of the insect choline acetyltransferase with acetyl-CoA and choline in a cell-free system with an $IC_{50}$ of 100 micro M or less;
9. A method for assaying pesticidal activity of a test substance, which comprises:
   (1) a first step of measuring the activity of a choline acetyltransferase selected from the following group A in a reaction system in which said choline acetyltransferase contacts with a test substance; and
   (2) a second step of evaluating the pesticidal activity of said test substance based on the difference obtained by comparing the activity measured in the first step with the activity of a control:

<Group A>
   (a) a protein comprising the amino acid sequence of SEQ ID NO: 1;

(b) a protein comprising an amino acid sequence with deletion, addition or substitution of one or more amino acids in the amino acid sequence of SEQ ID NO: 1, wherein said protein has choline acetyltransferase activity;

(c) a protein comprising an amino acid sequence that has sequence identity of 50% or more to the amino acid sequence of SEQ ID NO: 1, wherein said protein has choline acetyltransferase activity;

(d) a protein comprising an amino acid sequence that has sequence similarity of 75% or more to the amino acid sequence of SEQ ID NO: 1, wherein said protein has choline acetyltransferase activity;

(e) a protein comprising the amino acid sequence encoded by the nucleotide sequence of SEQ ID NO: 2 or 3;

(f) a protein comprising an amino acid sequence encoded by a nucleotide sequence that has sequence identity of 50% or more to the nucleotide sequence of SEQ ID NO: 2 or 3, wherein said protein has choline acetyltransferase activity;

(g) a protein comprising an amino acid sequence encoded by a polynucleotide, wherein said polynucleotide hybridizes under a stringent condition to a polynucleotide comprising a nucleotide sequence complementary to the nucleotide sequence of SEQ ID NO: 2 or 3, and wherein said protein has choline acetyltransferase activity;

(h) a protein comprising an amino acid sequence of an insect choline acetyltransferase; and (i) a protein comprising an amino acid sequence of a cotton aphid choline acetyltransferase;

10. A method for screening a pesticidal substance, which comprises selecting a substance having the pesticidal activity that is evaluated by the method of item 9;

11. A pesticidal agent which comprises a substance selected by the method of item 10 or agriculturally acceptable salts thereof as an active ingredient;

12. A method for controlling pests which comprises applying an effective amount of the pesticidal agent of item 5, 6, 7, 8 or 11 to the pest, habitat of the pest or plant to be protected from the pest;

13. A method for controlling pests which comprises:
identifying a substance having the pesticidal activity that is evaluated by the method of item 9, and
contacting the pest with the identified pesticidal substance;

14. An insect choline acetyltransferase comprising an amino acid sequence selected from the following group B:
<Group B>
(a) the amino acid sequence of SEQ ID NO: 1;

(b) an amino acid sequence with deletion, addition or substitution of one or more amino acids in the amino acid sequence of SEQ ID NO: 1, wherein said amino acid sequence has choline acetyltransferase activity;

(c) an amino acid sequence that has sequence identity of 50% or more to the amino acid sequence of SEQ ID NO: 1, wherein said amino acid sequence has choline acetyltransferase activity;

(d) an amino acid sequence that has sequence similarity of 75% or more to the amino acid sequence of SEQ ID NO: 1, wherein said amino acid sequence has choline acetyltransferase activity;

(e) the amino acid sequence encoded by the nucleotide sequence of SEQ ID NO: 2 or 3;

(f) an amino acid sequence encoded by a nucleotide sequence that has sequence identity of 50% or more to the nucleotide sequence of SEQ ID NO: 2 or 3, wherein said amino acid sequence has choline acetyltransferase activity;

(g) an amino acid sequence encoded by a polynucleotide, wherein said polynucleotide hybridizes under a stringent condition to a polynucleotide comprising a nucleotide sequence complementary to the nucleotide sequence of SEQ ID NO: 2 or 3, wherein said amino acid sequence has choline acetyltransferase activity; and (h) an amino acid sequence of a cotton aphid choline acetyltransferase;

15. Use of an insect choline acetyltransferase as a reagent that provides an indicator to evaluate pesticidal activity;

16. Use of an insect choline acetyltransferase of item 14 as a reagent that provides an indicator to evaluate pesticidal activity;

17. A polynucleotide which comprises a nucleotide sequence encoding an amino acid sequence of a choline acetyltransferase of item 14;

18. A polynucleotide according to item 17, which comprises the nucleotide sequence of SEQ ID NO: 2 or 3;

19. A polynucleotide which comprises a nucleotide sequence complementary to a nucleotide sequence of a polynucleotide of item 17 or 18;

20. A polynucleotide which comprises:
a partial nucleotide sequence of a polynucleotide of item 17 or 18; or
a nucleotide sequence complementary to said partial nucleotide sequence;

21. A polynucleotide according to item 20, which comprises the nucleotide sequence of SEQ ID NO: 4 or 5;

22. A method for obtaining a polynucleotide comprising a nucleotide sequence encoding an amino acid sequence of a choline acetyltransferase, which comprises:
amplifying a desired polynucleotide by polymerase chain reaction using as a primer a polynucleotide of item 20 or 21;
identifying the desired polynucleotide amplified; and
recovering the identified polynucleotide;

23. A method for obtaining a polynucleotide comprising a nucleotide sequence encoding an amino acid sequence of a choline acetyltransferase, which comprises:
detecting a desired polynucleotide by hybridization using as a probe a polynucleotide of item 19, 20 or 21;
identifying the desired polynucleotide detected; and
recovering the identified polynucleotide;

24. A circular polynucleotide comprising a nucleotide sequence of a polynucleotide of item 17 or 18, wherein said nucleotide sequence is operably linked to a bacteriophage promoter;

25. A circular polynucleotide according to item 24, wherein said promoter is a T7 RNA polymerase gene promoter;

26. A circular polynucleotide according to item 24 or 25, wherein said polynucleotide comprises a replication origin for autonomous replication in a host cell;

27. A method for producing a circular polynucleotide, which comprises ligating a polynucleotide of item 17 or 18 into a vector;

28. A transformant in which a polynucleotide of item 17 or 18 is introduced;

29. A transformant according to item 28, wherein said transformant is a transformed *E. coli*;

30. A method for producing a transformant, which comprises introducing a polynucleotide of item 17 or 18 into a host cell;

31. A method for producing a choline acetyltransferase, which comprises a step of culturing the transformant of item 28 or 29 and recovering a produced choline acetyltransferase;

32. Use of a choline acetyltransferase of item 14 or a polynucleotide of any one of items 17 to 21 as a research tool;

33. Use according to item 32, wherein the research tool is an experimental tool for screening a pesticidal substance; and 34. A system which comprises:
a means to input, store and manage a data information of an ability of test substances, wherein said ability is an ability to modulate the activity of an insect choline acetyltransferase;
a means to query and retrieve the data information based on a desired criterion; and
a means to display and output the result which is queried and retrieved.

MODES FOR CARRYING OUT THE INVENTION

The present invention will be explained in detail below.

In the present invention, the "pests" indicates small animals which cause harm or discomfort to life of the people by harming man and animals directly or by damaging crops. Examples thereof include arthropod such as insects, mites and ticks and Nematoda, and typical examples of which are as follows:

Hemiptera:
Delphacidae such as *Laodelphax striatellus*, *Nilaparvata lugens* and *Sogatella furcifera*, Deltocephalidae such as *Nephotettix cincticeps* and *Empoasca onukii*, Aphididae such as *Aphis gossypii* and *Myzus persicae*, Pentatomidae, Aleyrodidae such as *Trialeurodes vaporariorum*, *Bemisia tabaci* and *Bemisia argentifolli*, Coccidae, Tingidae, Psyllidae, etc.

Lepidoptera:
Pyralidae such as *Chilo suppressalis*, *Cnaphalocrocis medinalis*, *Ostrinia nubilalis* and *Parapediasia teterrella*, Noctuidae such as *Spodoptera litura*, *Spodoptera exigua*, *Pseudaletia separata*, *Mamestra brassicae*, *Agrotis ipsilon*, *Trichoplusia* spp., *Heliothis* spp., *Helicoverpa* spp. and *Earias* spp., Pieridae such as *Pieris rapae crucivora*, Tortricidae such as *Adoxophyes orana fasciata*, *Grapholita molesta* and *Cydia pomonella*, Carposimidae such as *Carposina niponensis*, Bucculatriciidae such as *Lyonetia clerkella*, Gracillariidae such as *Phyllonorycter ringoniella*, Phyllocnistidae such as *Phyllocnistis citrella*, Yponomeutidae such as *Plutella xylostella*, Gelechiidae such as *Pectinophora gossypiella*, Arctiidae, Tineidae, etc.

Diptera:
*Culex* such as *Culex pipiens pallens*, *Cules tritaeniorhynchus* and *Culex quinquefasciatus*, *Aedes* such as *Aedes aegypti* and *Aedes albopictus*, Anopheles such as *Anophelinae sinensis*, Chironomidae, Muscidae such as *Musca domestica* and *Muscina stabulans*, Calliphoridae, Sarcophagidae, *Fannia canicularis*, Anthomyiidae such as *Delia Platura* and *Delia antigua*, Trypetidae, Drosophilidae, Psychodidae, Simuliidae, Tabanidae, Stomoxyidae, Agromyzidae, etc.

Coleoptera:
*Diabrotica* such as *Diabrotica virgifera virgifera* and *Diabrotica undecimpunctata howardi*, Scarabaeidae such as *Anomala cuprea* and *Anomala rufocuprea*, Curculionidae such as *Sitophilus zeamais*, *Lissorphoptrus oryzophilus* and *Calosobruchys chinensis*, Tenebrionidae such as *Tenebrio molitor* and *Tribolium castaneum*, Chrysomelidae such as *Oulema oryzae*, *Aulacophora femoralis*, *Phyllotreta striolata* and *Leptinotarsa decemlineata*, Anobiidae, *Epilachna* spp. such as *Epilachna vigintioctopunctata*, Lyctidae, Bostrychidae, Cerambycidae, *Paederus fuiscipes*, etc.

Thysanoptera:
Thripidae such as *Thrips* spp. including *Thrips palmi*, *Frankliniella* spp. including *Frankliniella occidentalis* and *Sciltothrips* spp. including *Sciltothrips dorsalis*, Phlaeothripidae, etc.

Hymenoptera:
Tenthredinidae, Formicidae, Vespidae, etc.

Dictyoptera:
Blattidae, Blattellidae, etc.

Orthoptera:
Acrididae, Gryllotalpidae etc.

Siphonaptera:
*Pulex irritans*, etc.

Anoplura:
*Pediculus humanus capitis*, etc.

Isoptera:
Termitidae, etc.

Acarina:
Tetranychidae such as *Tetranychus urticae*, *Tetranychus kanzawai*, *Panonychus citri*, *Panonychus ulmi*, and *Oligonychus* spp., Eriophyidae such as *Aculops pelekassi* and *Aculus schlechtendali*, Tarsonemidae such as *Polyphagotarsonemus latus*, Tenuipalpidae, Tuckerellidae, Ixodidae such as *Haemaphysalis longicornis*, *Haemaphysalis flava*, *Dermacentor taiwanicus*, *Ixodes ovatus*, *Ixodes persulcatus* and *Boophilus microplus*, Acaridae such as *Tyrophagus putrescentiae*, Dermanyssidae, Cheyletidae such as *Dermatophagoides farinae* and *Dermatophagoides ptrenyssnus*, such as *Cheyletus eruditus*, *Cheyletus malaccensis* and *Cheyletus moorei*, *Dermanyssus* spp., etc.

Nematodes:
*Pratylenchus coffeae*, *Pratylenchus fallax*, *Heterodera glycines*, *Globodera rostochiensis*, *Meloidogyne hapla*, *Meloidogyne incognita*, etc.

In the present invention, the "modulate physiological condition of pests" indicates changing condition such as various phenomena in a living body which are maintained for living in pests, for example, function such as aspiration, digestion, secretion, body liquid circulation, metabolism and neurotransmission, or mechanism thereof into condition apart from usual condition. Examples include changing condition by cessation of aspiration so that oxygen necessary for internal metabolism of pests will not be supplied, and changing condition by cessation of function of neurotransmission of pests so that various movements of pests will be ceased.

In the present invention, the "agent which modulates physiological condition of pests" is an agent which can modulate physiological condition of pests when being applied to pests.

In the present invention, the "insect choline acetyltransferase" indicates a choline acetyltransferase that occurs in insect, among choline acetyltransferase present in various organisms. Herein, insect is an animal classified under Animalia, Arthropoda, Insecta, and examples of which include arthropod of the order Protura, Collembola, Diplura, Thysanura, Ephemeroptera, Odonata, Plecoptera, Grylloblattodea, Orthoptera, Phasmatodea, Dermaptera, Mantodea, Blattaria, Isoptera, Embioptera, Psocoptera, Mallophaga, Anoplura, Thysanoptera, Hemiptera, Neuroptera, Mecoptera, Trichoptera, Lepidoptera, Coleoptera, Diptera, Hymenoptera, Siphonaptera, Strepsiptera, and the like.

Choline acetyltransferase (acetyl CoA:choline O-acetyltransferase, EC 2.3.1.6; synonym: Choline acetylase, Choline O-acetyltransferase; ChAT) catalyzes reaction to synthesize the neurotransmitter acetylcholine from its precursors, acetyl-coenzyme A (acetyl-CoA) and choline.

The activity of choline acetyltransferase can be monitored using a radiometric based in vitro assay. For example, as reported by Heo Ho-Jin et al., Biosci. Biotechnol. Biochem., 67(6), 1284-1291, 2003, after choline acetyltransferase-catalyzed reaction on substrates of acetyl-CoA and choline using radiolabelled $^{14}$C-acetyl-CoA, the formed $^{14}$C-acetylcholine is extracted with tetraphenylboron (TPB). The 2 phases are separated and the radioactivity of the upper phase is measured in a liquid scintillation counter.

Another assay that can be used to measure the choline acetyltransferase activity is an absorbance assay. The principle of the absorbance assay is that choline acetyltransferase activity can be determined by measuring the free Coenzyme A (CoA) formed by choline acetyltransferase reaction using 5,5'-dithio-bis(2-nitrobenzoic acid) (DTNB) reagent. DTNB reacts with free thiol groups in solution to produce 5-thio-2-nitrobenzoic acid (TNB). TNB is yellow and has absorption maximum at 412 nm. This colored TNB can then be measured by absorbancy at 405 nm.

Of the assays of choline acetyltransferase activity described above, the assay using DTNB is preferable for measuring choline acetyltransferase activity in a large number of samples mechanically and efficiently. Specifically, after choline acetyltransferase reaction on substrates of acetyl-CoA and choline, DTNB is added and then the free CoA formed by the enzyme reaction is quantified by measuring absorbancy at 405 nm.

The activity of insect choline acetyltransferase can be measured by methods similar to that described above.

Several amino acid sequences of choline acetyltransferase have been identified in different insect species such as *D. melanogaster* (isoform A, accession No. NP_477004; and isoform B, accession No. NP_996239), *Tribolium castaneum* (accession No. XP_975503), *Apis mellifera* (accession No. XP_392463), *Aedes aegypti* (accession No. XP_001660851) and *Anopheles gambiae* (accession No. XP_312586), which can be found in public databases.

Also, several nucleotide sequences of choline acetyltransferase genes have been identified in different insect species, such as *D. melanogaster* (isoform A, accession No. NM_057656; isoform B, accession No. NM_206517), *Tribolium castaneum* (accession No. XM_970410), *Apis mellifera* (accession No. XM_392463), *Aedes aegypti* (accession No. XM_001660801) and *Anopheles gambiae* (accession No. XM_312586), which can be found in public databases.

In addition, according to the methods described below, an amino acid sequence of choline acetyltransferase and a nucleotide sequence of choline acetyltransferase gene can be identified from a cotton aphid. The identified amino acid sequence of cotton aphid choline acetyltransferase is shown in SEQ ID NO: 1, and the nucleotide sequence of cotton aphid choline acetyltransferase gene is shown in SEQ ID NO: 2.

Several amino acid sequences of choline acetyltransferase have been identified in animals other than insect, such as *Ceanorhabditis elegans* (accession No. AAB88370) and *Homo sapiens* (accession No. NP065574), which can be found in public databases. Also, several nucleotide sequences of choline acetyltransferase genes have been identified in animals other than insect, such as *Ceanorhabditis elegans* (accession No. ZC416.8) and *Homo sapiens* (accession No. NM_020549), which can be found in public databases.

Table 1 shows Sequence identity of the amino acid sequence of cotton aphid choline acetyltransferase (SEQ ID NO: 1) and the nucleotide sequence of cotton aphid choline acetyltransferase gene (SEQ ID NO: 2) with the sequences of choline acetyltransferase and gene thereof found in other animals.

TABLE 1

| Origin of sequence | Identity of amino acid sequence (%) vs SEQ ID NO: 1 | Identity of nucleotide sequence (%) vs SEQ ID NO: 2 |
| --- | --- | --- |
| Tribolium castaneum | 48.8 | 70.6 |
| Aedes aegypti | 44.7 | 69.9 |
| Anopheles gambiae | 44.5 | 71.4 |
| Apis mellifera | 43.5 | 70.0 |
| Drosophila melanogaster | 43.2 | 70.1 |
| Strongylocentrotus purpuratus | 40.0 | 69.5 |
| Gallus gallus | 39.8 | 69.1 |
| Homo sapiens | 38.7 | 69.4 |
| Canis familiaris | 38.6 | 68.9 |
| Danio renio | 37.4 | 67.2 |
| Xenopus tropicalis | 37.1 | 67.0 |
| Bos taurus | 36.7 | 66.2 |

An ability to modulate the activity of an insect choline acetyltransferase refers to an ability to increase or decrease activity of an insect choline acetyltransferase, that is, means an ability to activate a choline acetyltransferase, or an ability to inhibit activity of a choline acetyltransferase. And, a test substance may be added to the reaction system for measuring choline acetyltransferase activity to investigate influence of the test substance on the choline acetyltransferase activity.

Several substances having an ability to inhibit activity of a choline acetyltransferase, such as Bromoacetylcholine (Sastry and Janson, J. Ocular Pharmacol., 10:203-215, 1994), Theaflavin (Sugatani et al., Int. Arch. Allergy Immunol., 134: 17-28, 2004) and α-NETA (Sastry et al., J. Pharmacol. Exp. Ther., 245:72-80, 1988) have been known.

An $IC_{50}$ value of a test substance in the reaction means a concentration of a test substance at which 50% of the activity of the reaction with no test substance is inhibited. The $IC_{50}$ value of a test substance can be determined by adding test substances of different concentrations to the choline acetyltransferase activity measuring reaction system, measuring the choline acetyltransferase activity (response) at each concentration of added test substance (dose), producing a dose-response curve, and calculating a concentration of the added test substance, at which the choline acetyltransferase activity is 50% inhibited. More specifically, a dose-response curve may be produced using 4 Parameter Logistic Model or Sigmoidal Dose-Response Model:

$$f(x) = (A + ((B - A/(1 + ((C/x)^\wedge D))))$$

$$f(x) = A + \frac{B - A}{1 + (C/x)^D}$$

to calculate the $IC_{50}$. Practically, the $IC_{50}$ value may be calculated using XLfit (manufactured by IDBS) which is a commercially available calculating software.

An agent that has an ability to modulate the activity of an insect choline acetyltransferase is an agent containing as an active ingredient a substance having an ability to modulate the activity of an insect choline acetyltransferase.

In the present invention, the "agent that modulates physiological condition of pests, wherein the agent has an ability to modulate the activity of an insect choline acetyltransferase" is an agent having an ability to modulate the activity of insect choline acetyltransferase identified by the aforementioned measuring method, and means an agent that can modulate physiological condition of pests. Preferable examples of the agent include an agent in which an insect choline acetyltransferase is a cotton aphid choline acetyltransferase. In addition, preferable examples of the agent include an agent in which an agent that modulates physiological condition of pests is a pesticidal agent. In addition, preferable examples of the agent include an agent in which an ability to modulate the activity of an insect choline acetyltransferase is an ability to inhibit a reaction using acetyl-CoA and choline as substrates.

In the present invention, the "pesticidal agent" indicates an agent having an ability to control the pests.

Examples of a method for measuring an ability to control pests include, in addition to the methods disclosed in the present invention, a method of measuring pesticidal activity on the pests. Specifically, for example, the pesticidal activity can be measured according to the following method.

According to the method described in Handbook of Insect Rearing Vol. 1 (Elsevier Science Publisers 1985), pp. 35 to pp. 36 except that a sterilized artificial feed having the composition shown in Table 2 is prepared, and a solution of a test agent in DMSO is added at 0.5% by volume of the artificial feed and is mixed, a cotton aphid is reared, the number of surviving cotton aphids is investigated after 6 days, and a controlling value is obtained according to the following equation.

TABLE 2

| | (mg/100 ml) |
|---|---|
| Amino acid | |
| L-Alanine | 100.0 |
| L-arginine | 275.0 |
| L-Asparagine | 550.0 |
| L-Aspartic acid | 140.0 |
| L-cysteine (hydrochloride) | 40.0 |
| L-glutamic acid | 140.0 |
| L-glutamine | 150.0 |
| L-glycine | 80.0 |
| L-histidine | 80.0 |
| L-isoleucine | 80.0 |
| L-leucine | 80.0 |
| L-lysine (hydrochloride) | 120.0 |
| L-methionine | 80.0 |
| L-phenylalanine | 40.0 |
| L-proline | 80.0 |
| L-serine | 80.0 |
| L-threonine | 140.0 |
| L-tryptophan | 80.0 |
| L-tyrosine | 40.0 |
| L-valine | 80.0 |
| Vitamins | |
| Ascorbic acid | 100.0 |
| Biotin | 0.1 |
| Calcium pantothenate | 5.0 |
| Choline chloride | 50.0 |
| Inositol | 50.0 |
| Nicotinic acid | 10.0 |
| Thiamine | 2.5 |
| Others | |
| Sucrose | 12500.0 |
| Dipotassium hydrogen phosphate | 1500.0 |
| Magnesium sulfate | 123.0 |
| Cupric chloride | 0.2 |
| Ferric chloride | 11.0 |
| Manganese chloride | 0.4 |
| Zinc sulfate (anhydrous) | 0.8 |
| Adjusted to pH 6.8 | |

Controlling value (%)={1−($Cb$×$Tai$)/($Cai$×$Tb$)}×100

Letters in the equation represent the following meanings.
Cb: Number of surviving worms before treatment in non-treating section Cai: Number of surviving worms at observation in non-treated section
Tb: Number of surviving worms before treatment in non-treated section
Tai: Number of surviving worms at observation in a treated section It may be said that a test agent exhibiting a significantly high controlling value has the pesticidal activity. Preferably, it may be determined that a test agent having the controlling value of 30% or more has substantial pesticidal activity, and it may be determined that a test agent having the controlling value of less than 30% has no substantial pesticidal activity.

The pesticidal agent in the present invention contains a chemical substance having an ability to modulate the activity of insect choline acetyltransferase or an agriculturally acceptable salt thereof as an active ingredient.

In the present invention, an agriculturally acceptable salt refers to a salt in such a form that preparation of a controlling agent and application of the preparation do not become impossible, and may be a salt in any form. Specifically, examples of the salt include acid addition salts with mineral acids such as hydrochloric acid, hydrobromic acid, hydriodic acid, sulfuric acid, nitric acid, and phosphoric, organic acids such as formic acid, acetic acid, propionic acid, oxalic acid, malonic acid, succinic acid, fumaric acid, maleic acid, lactic acid, malic acid, tartaric acid, citric acid, methanesulfonic acid, and ethansulfonic acid, or acidic amino acids such as aspartic acid and glutamic acid; salts with inorganic bases such as sodium, potassium, magnesium, and aluminum, organic bases such as methylamine, ethylamine, and ethanolamine, or basic amino acids with lysine and ornithine; and an ammonium salts.

In the present invention, the "pesticidal agent which comprises a substance having an ability to modulate the activity of an insect choline acetyltransferase or a an agriculturally acceptable salt thereof as an active ingredient" means an agent which can control pests by containing a substance having an ability to modulate the activity of insect choline acetyltransferase identified in the measuring method or an agriculturally acceptable salt thereof as an active ingredient. Preferable examples of the substance include a compound having an ability to inhibit a reaction of a choline acetyltransferase with acetyl-CoA and choline. More preferable examples of the substance include a substance having an ability to inhibit the reaction of the insect choline acetyltransferase with acetyl-CoA and choline in a cell-free system, wherein in the presence of the substance of 10 μM or more the activity of the choline acetyltransferase is lower than that in the absence of the substance. In addition, further preferable examples of the substance include a substance having an ability to inhibit a reaction of the insect choline acetyltransferase with acetyl-CoA and choline in a cell-free system with an $IC_{50}$ of 100 μM or less.

In the present invention, the "method for assaying pesticidal activity of a test substance, which comprises a first step of measuring the activity of a choline acetyltransferase selected from the group A in a reaction system in which the choline acetyltransferase contacts with a test substance, and a second step of evaluating the pestcidal activity of the test substance based on the difference obtained by comparing the activity measured in the first step with the activity of a control" indicates a method characterized by comprising the first step and the second step in various methods for assaying a pesticidal ability of a test substance.

Herein, the group A indicates:
(a) a protein comprising the amino acid sequence of SEQ ID NO: 1;

(b) a protein comprising an amino acid sequence with deletion, addition or substitution of one or more amino acids in the amino acid sequence of SEQ ID NO: 1, wherein said protein has choline acetyltransferase activity;

(c) a protein comprising an amino acid sequence that has sequence identity of 50% or more to the amino acid sequence of SEQ ID NO: 1, wherein said protein has choline acetyltransferase activity;

(d) a protein comprising an amino acid sequence that has sequence similarity of 75% or more to the amino acid sequence of SEQ ID NO: 1, wherein said protein has choline acetyltransferase activity;

(e) a protein comprising the amino acid sequence encoded by the nucleotide sequence of SEQ ID NO: 2 or 3;

(f) a protein comprising an amino acid sequence encoded by a nucleotide sequence that has sequence identity of 50% or more to the nucleotide sequence of SEQ ID NO: 2 or 3, wherein said protein has choline acetyltransferase activity;

(g) a protein comprising an amino acid sequence encoded by a polynucleotide, wherein said polynucleotide hybridizes under a stringent condition to a polynucleotide comprising a nucleotide sequence complementary to the nucleotide sequence of SEQ ID NO: 2 or 3, and wherein said protein has choline acetyltransferase activity;

(h) a protein comprising an amino acid sequence of an insect choline acetyltransferase; and (i) a protein comprising an amino acid sequence of a cotton aphid choline acetyltransferase.

The first step is a step of measuring the activity of a choline acetyltransferase in the state where a choline acetyltransferase is contacted with a test substance by adding the test substance to the aforementioned various choline acetyltransferase activity measuring reaction systems.

The second step is a step of comparing the activity at measurement of a test substance with the substance of a control, and evaluating a pesticidal ability based on the difference. Herein, a control means, for example, in the case where a test substance dissolved in a solvent is added to the reaction system, a test section in which only a solvent same as that used to dissolve the test substance is added.

A choline acetyltransferase used in a method for assaying a pestcidal ability possessed by a test substance, having the first step and the second step, is a protein shown in the group A. Among proteins of the group A, a difference which can be recognized between an amino acid sequence of protein represented by (a) and amino acid sequences of proteins represented by (b), (c), (e), (f), (g), (h) and (i) is deletion, substitution, addition or the like of a part of amino acids. These include, for example, deletion due to processing which the protein having an amino acid sequence represented by (a) undergoes in a cell. In addition, examples include deletion, substitution, addition and the like of an amino acid generated by naturally occurring gene mutation due to a spices difference or an individual difference of an organism from which the protein is derived, or gene mutation which is artificially introduced by a site-directed mutagenesis, a random mutagenesis, mutation treatment or the like.

The number of amino acids undergoing the deletion, substitution, addition or the like may be the number in a range that the choline acetyltransferase activity of a choline acetyltransferase can be found out. In addition, examples of substitution of an amino acid include substitution with an amino acid which is similar in characteristic in hydrophobicity, charge, pH and steric structure. Specific examples of the substitution include substitution in an group of (1) glycine, alanine; (2) valine, isoleucine, leucine; (3) aspartic acid, glutamic acid, asparagine, glutamine, (4) serine, threonine; (5) lysine, arginine; (6) phenylalanine, tyrosine and the like.

Examples of a procedure of artificially introducing the deletion, addition or substitution of an amino acid (hereinafter, collectively referred to as alteration of amino acid in some cases) include a procedure of introducing site-directed mutation into a DNA encoding an amino acid sequence represented by (a) and, thereafter, expressing this DNA by a conventional method. Herein, examples of a site-directed mutagenesis include a method utilizing amber mutation (gapped duplex method, Nucleic Acids Res., 12, 9441-9456 (1984)), a method by PCR using primers for mutation introduction, and the like. In addition, examples of a procedure of artificially altering an amino acid include a procedure of randomly introducing mutation into a DNA encoding an amino acid sequence represented by (a) and, thereafter, expressing this DNA by a conventional method. Herein, examples of a method of randomly introducing mutation include a method of performing PCR using a DNA encoding any of the aforementioned amino acid sequences as a template, and using a primer pair which can amplify each full length DNA at reaction condition under which an addition amount of each of dATP, dTTP, dGTP and dCTP used as substrates is changed from a conventional concentration, or at reaction condition under which a concentration of $Mg^{2+}$ promoting a polymerase reaction is increased from a conventional concentration. Examples of the procedure of PCR include a method described, for example, in Method in Molecular Biology, (31), 1994, 97-112. Another example includes a method described in WO 0009682.

As used herein, the "sequence identity" means the identity between two nucleotide sequences or two amino acid sequences. The "sequence identity" is determined by comparing the two sequences in an optimal alignment across the entire region of the sequence under comparison. The optimal alignment of the nucleotide sequence or amino acid sequence under comparison may allow for additions or deletions (for example, gaps). The sequence identity may be calculated by analyzing homology using programs such as FASTA [Pearson & Lipman, Proc. Natl. Acad. Sci. USA. 4, 2444-2448 (1998)], BLAST [Altschul et al. Journal of Molecular Biology, 215, 403-410 (1990)], and CLUSTAL W [Thompson, Higgins & Gibson, Nucleic Acid Research, 22, 4673-4680 (1994a)] to prepare an alignment. These programs are available from the website (www.ddbj.nig.ac.jp) of the DNA Data Bank of Japan [the international DNA data bank managed by the Center for Information Biology and DNA Data Bank of Japan; CIB/DDBJ]. The sequence identity may also be analyzed using commercially available sequence analysis software. In particular, the sequence identity may be calculated by analyzing homology using GENETYX-WIN Ver. 5 (manufactured by Software Development Co., Ltd.) by the Lipman-Pearson method (Lipman, D. J. and Pearson, W. R., Science, 227, 1435-1441, (1985)) to prepare an alignment.

When two optimally aligned amino acid sequences as described above have a difference in sequence as a result of conservative amino acid substitution, the "sequence similarity" is used in order to express the conservation of substituted amino acids. It may be said that the sequence similarity exists between sequence pairs which have differences in sequence resulting from conservative amino acid substitutions. This type of sequence similarity can be analyzed using programs such as FASTA above. Amino acids may be divided into four groups of hydrophobic amino acids, neutral amino acids, acidic amino acids and basic amino acids. The substitution of an amino acid by another amino acid of the same group is termed conservative amino acid substitution.

Group of hydrophobic amino acids includes alanine (A), valine (V), leucine (L), isoleucine (I), methionine (M), tryptophan (W), phenylalanine (F) and proline (P).

Group of neutral amino acids includes glycine (G), serine (S), threonine (T), cysteine (C), tyrosine (Y), asparagine (N) and glutamine (Q).

Group of acidic amino acids includes aspartic acid (D) and glutamic acid (E).

Group of basic amino acids includes lysine (K), histidine (H) and arginine (R).

Examples of the "stringent condition" described in (g) include condition under which, in hybridization performed according to a conventional method described in Sambrook J., Frisch E. F., Maniatis T., Molecular Cloning 2nd edition, Cold Spring Harbor Laboratory press, for example, a hybrid is formed at 45° C. in a solution containing 6×SSC (a solution containing 1.5 m NaCl and 0.15 m trisodium citrate is 10×SSC) and, thereafter, this is washed with 2×SSC at 50° C. (Molecular Biology, John Wiley & Sons, N.Y. (1989), 6.3.1-6.3.6). A salt concentration in a washing step can be selected from condition from 2×SSC (low stringent condition) to 0.2× SSC (high stringent condition). A temperature in a washing step can be selected, for example, from condition from room temperature (low stringent condition) to 65° C. (high stringent condition). Alternatively, both of a salt concentration and a temperature can be changed.

A protein described in (i) indicates a choline acetyltransferase presents in a cotton aphid among an insect choline acetyltransferase, and includes a protein comprising the amino acid sequence described in (a).

While proteins of the group A include a protein described in (c) which comprises an amino acid sequence that has sequence identity of 50% or more to the amino acid sequence of SEQ ID NO: 1 and which has choline acetyltransferase activity, a protein having choline acetyltransferase activity and comprising an amino acid sequence that has sequence identity of at least 55, 60, 65, 70, 75 or 80% to the amino acid sequence of SEQ ID NO: 1 may be preferably used, and a protein having choline acetyltransferase activity and comprising an amino acid sequence that has sequence identity of at least 85, 90 or 95% to the amino acid sequence of SEQ ID NO: 1 may be highly preferred.

While proteins of the group A also include a protein described in (d) which comprises an amino acid sequence that has sequence similarity of 75% or more to the amino acid sequence of SEQ ID NO: 1 and which has choline acetyltransferase activity, a protein having choline acetyltransferase activity and comprising an amino acid sequence that has sequence similarity of at least 80% to the amino acid sequence of SEQ ID NO: 1 may be preferably used, and a protein having choline acetyltransferase activity and comprising an amino acid sequence that has sequence similarity of at least 85, 90 or 95% to the amino acid sequence of SEQ ID NO: 1 may be highly preferred.

A substance having pesticidal ability can be screened by using a method of assaying pesticidal ability by measuring pesticidal ability or controlling effect on the aforementioned pests.

Alternatively, a substance having pesticidal ability can be also screened by the aforementioned method of assaying pesticidal ability using a choline acetyltransferase. Specifically, when it has been identified that pesticidal ability of a test substance is a certain value or more, or a certain value or less by the aforementioned method of assaying pesticidal ability using a choline acetyltransferase, a substance having pesticidal ability can be screened by selecting the substance.

Since a substance selected by the screening method has pesticidal ability, it can be used as a pesticidal agent containing the substance or an agriculturally acceptable salt thereof as an active ingredient.

Control of pests can be usually performed by application of an effective amount of the pesticidal agent to a crop to be protected, a pest, or a habitat of a pest.

When the pesticidal agent is used for agriculture and forestry, its application amount is usually 0.1 to 1000 g in terms of an amount of the pesticidal agent per 1000 m$^2$. When the pesticidal agent is formulated into an emulsion, a water-dispersible powder, a flowable preparation, a microcapsule preparation or the like, the agent is usually applied by diluting with water to an active ingredient concentration of 1 to 10,000 ppm, and spraying this and, when the pesticidal agent is formulated into a granule, a powder or the like, the agent is usually applied as it is.

The pesticidal agent can be used by foliage-treating a plant such as a crop and the like which should be protected from pests, and can be also used by treating a seedbed before a plantlet of a crop is transplanted, or a planting hole or a strain base at planting. Further, for the purpose of controlling pests habiting a soil of a cultivating land, the agent may be used by treating the soil. Alternatively, the agent may be used by a method of winding a resin preparation which has been processed to a sheet or a string, on a crop, stretching the preparation near a crop and/or spreading on a soil surface of a strain base.

When the pesticidal agent is used as a pest controlling agent for preventing an epidemic, an emulsion, a water-dispersible powder, a flowable or the like is usually applied by diluting with water so that an active ingredient concentration will become 0.01 to 10,000 ppm, and an oily agent, an aerosol, a fumigant, a poison bait or the like is applied as it is.

Examples of one utility of the pesticidal agent include control of an external parasite of a livestock such as cattle, sheep, goat, and chicken, or a small animal such as dog, cat, rat, and mouse, in this case, the agent can be administered to an animal by the veterinarily known method. As a specific administration method, when systemic control is intended, the agent is administered, for example, by a tablet, mixing in feed, suppository, injection (intramuscular, subcutaneous, intravenous, intraperitoneal etc.) and the like, when non-systemic control is intended, the agent is used by a method of spraying an oily agent or an aqueous liquid agent, performing pour on or spot on treatment, washing an animal with a shampoo preparation or attaching a resin preparation which has been processed into a necklace or a ear tag to an animal. An amount of the pesticidal agent when administered to an animal body is usually in a range of 0.1 to 1,000 mg as expressed by total amount of a compound A and a compound B per 1 kg of an animal.

An application amount and an application concentration of them may be both different depending on the situations such as a kind of a preparation, an application time, an application place, an application method, a kind of a pest, a damage degree and the like, can be increased or decreased regardless of the aforementioned range, and can be appropriately selected.

The aforementioned pesticidal agent can be used in the method of controlling pests as described above.

In addition, a pest can be also controlled by identifying a substance having a pesticidal ability evaluated by the aforementioned method of assaying pesticidal ability possessed by a pest substance, comprising a first step and a second step using a choline acetyltransferase selected from group A, and contacting the identified substance having pesticidal ability with a pest. Herein, for contacting an identified substance having pesticidal ability with a pest, the aforementioned preparation method, application method and the like can be used.

An amino acid sequence shown in the group B is an amino acid sequence of insect choline acetyltransferase comprising any amino acid sequence of the following (a) to (h):

(a) the amino acid sequence of SEQ ID NO: 1;

(b) an amino acid sequence with deletion, addition or substitution of one or more amino acids in the amino acid sequence of SEQ ID NO: 1, wherein said amino acid sequence has choline acetyltransferase activity;

(c) an amino acid sequence that has sequence identity of 50% or more to the amino acid sequence of SEQ ID NO: 1, wherein said amino acid sequence has choline acetyltransferase activity;

(d) an amino acid sequence that has sequence similarity of 75% or more to the amino acid sequence of SEQ ID NO: 1, wherein said amino acid sequence has choline acetyltransferase activity;

(e) the amino acid sequence encoded by the nucleotide sequence of SEQ ID NO: 2 or 3;

(f) an amino acid sequence encoded by a nucleotide sequence that has sequence identity of 50% or more to the nucleotide sequence of SEQ ID NO: 2 or 3, wherein said amino acid sequence has choline acetyltransferase activity;

(g) an amino acid sequence encoded by a polynucleotide, wherein said polynucleotide hybridizes under a stringent condition to a polynucleotide comprising a nucleotide sequence complementary to the nucleotide sequence of SEQ ID NO: 2 or 3, wherein said amino acid sequence has choline acetyltransferase activity; and (h) an amino acid sequence of a cotton aphid choline acetyltransferase.

Among amino acid sequences of the group B, a difference which can be recognized between an amino acid sequence represented by (a) and amino acid sequences represented by (b), (c), (e), (f), (g) and (h) is deletion, substitution, addition or the like of a part of amino acids. These include, for example, deletion due to processing which the protein having an amino acid sequence represented by (a) undergoes in a cell. In addition, examples include deletion, substitution, addition and the like of an amino acid generated by naturally occurring gene mutation due to a spices difference or an individual difference of an organism from which the protein is derived, or gene mutation which is artificially introduced by a site-directed mutagenesis, a random mutagenesis, mutation treatment or the like.

The number of amino acids undergoing the deletion, substitution, addition or the like may be the number in a range that the peptidase activity of a choline acetyltransferase can be found out. In addition, examples of substitution of an amino acid include substitution with an amino acid which is similar in characteristic in hydrophobicity, charge, pH and steric structure. Specific examples of the substitution include substitution in an group of (1) glycine, alanine; (2) valine, isoleucine, leucine; (3) aspartic acid, glutamic acid, asparagine, glutamine, (4) serine, threonine; (5) lysine, arginine; (6) phenylalanine, tyrosine and the like.

Examples of a procedure of artificially introducing the deletion, addition or substitution of an amino acid (hereinafter, collectively referred to as alteration of amino acid in some cases) include a procedure of introducing site-directed mutation into a DNA encoding an amino acid sequence represented by (a) and, thereafter, expressing this DNA by a conventional method. Herein, examples of a site-directed mutagenesis include a method utilizing amber mutation (gapped duplex method, Nucleic Acids Res., 12, 9441-9456 (1984)), a method by PCR using primers for mutation introduction, and the like. In addition, examples of a procedure of artificially altering an amino acid include a procedure of randomly introducing mutation into a DNA encoding an amino acid sequence represented by (a) and, thereafter, expressing this DNA by a conventional method. Herein, examples of a method of randomly introducing mutation include a method of performing PCR using a DNA encoding any of the aforementioned amino acid sequences as a template, and using a primer pair which can amplify each full length DNA at reaction condition under which an addition amount of each of dATP, dTTP, dGTP and dCTP used as substrates is changed from a conventional concentration, or at reaction condition under which a concentration of $Mg^{2+}$ promoting a polymerase reaction is increased from a conventional concentration. Examples of the procedure of PCR include a method described, for example, in Method in Molecular Biology, (31), 1994, 97-112. Another example includes a method described in WO 0009682.

As used herein, the "sequence identity" means the identity between two nucleotide sequences or two amino acid sequences. The "sequence identity" is determined by comparing the two sequences in an optimal alignment across the entire region of the sequence under comparison. The optimal alignment of the nucleotide sequence or amino acid sequence under comparison may allow for additions or deletions (for example, gaps). The sequence identity may be calculated by analyzing homology using programs such as FASTA [Pearson & Lipman, Proc. Natl. Acad. Sci. USA. 4, 2444-2448 (1998)], BLAST [Altschul et al. Journal of Molecular Biology, 215, 403-410 (1990)], and CLUSTAL W [Thompson, Higgins & Gibson, Nucleic Acid Research, 22, 4673-4680 (1994a)] to prepare an alignment. These programs are available from the website (www.ddbj.nig.ac.jp) of the DNA Data Bank of Japan [the international DNA data bank managed by the Center for Information Biology and DNA Data Bank of Japan; CIB/DDBJ]. The sequence identity may also be analyzed using commercially available sequence analysis software. In particular, the sequence identity may be calculated by analyzing homology using GENETYX-WIN Ver. 5 (manufactured by Software Development Co., Ltd.) by the Lipman-Pearson method (Lipman, D. J. and Pearson, W. R., Science, 227, 1435-1441, (1985)) to prepare an alignment.

When two optimally aligned amino acid sequences as described above have a difference in sequence as a result of conservative amino acid substitution, the "sequence similarity" is used in order to express the conservation of substituted amino acids. It may be said that the sequence similarity exists between sequence pairs which have differences in sequence resulting from conservative amino acid substitutions. This type of sequence similarity can be analyzed using programs such as FASTA above. Amino acids may be divided into four groups of hydrophobic amino acids, neutral amino acids, acidic amino acids and basic amino acids. The substitution of an amino acid by another amino acid of the same group is termed conservative amino acid substitution.

Group of hydrophobic amino acids includes alanine (A), valine (V), leucine (L), isoleucine (I), methionine (M), tryptophan (W), phenylalanine (F) and proline (P).

Group of neutral amino acids includes glycine (G), serine (S), threonine (T), cysteine (C), tyrosine (Y), asparagine (N) and glutamine (Q).

Group of acidic amino acids includes aspartic acid (D) and glutamic acid (E).

Group of basic amino acids includes lysine (K), histidine (H) and arginine (R).

Examples of the "stringent condition" described in (g) include condition under which, in hybridization performed according to a conventional method described in Sambrook J., Frisch E. F., Maniatis T., Molecular Cloning 2nd edition, Cold Spring Harbor Laboratory press, for example, a hybrid is formed at 45° C. in a solution containing 6×SSC (a solution containing 1.5 m NaCl and 0.15 m trisodium citrate is 10×SSC) and, thereafter, this is washed with 2×SSC at 50° C. (Molecular Biology, John Wiley & Sons, N.Y. (1989), 6.3.1-6.3.6). A salt concentration in a washing step can be selected from condition from 2×SSC (low stringent condition) to 0.2× SSC (high stringent condition). A temperature in a washing step can be selected, for example, from condition from room temperature (low stringent condition) to 65° C. (high stringent condition). Alternatively, both of a salt concentration and a temperature can be changed.

A protein having an amino acid sequence described in (h) indicates a choline acetyltransferase presents in a cotton aphid among an insect choline acetyltransferase, and includes a protein comprising an amino acid sequence described in (a).

While amino acid sequences of the group B include an amino acid sequence described in (c) which has sequence identity of 50% or more to the amino acid sequence of SEQ ID NO: 1 and which has choline acetyltransferase activity, an amino acid sequence having choline acetyltransferase activity and having sequence identity of at least 55, 60, 65, 70, 75 or 80% to the amino acid sequence of SEQ ID NO: 1 may be preferably used, and an amino acid sequence having choline acetyltransferase activity and having sequence identity of at least 85, 90 or 95% to the amino acid sequence of SEQ ID NO: 1 may be highly preferred.

While amino acid sequences of the group B also include an amino acid sequence described in (d) which has sequence similarity of 75% or more to the amino acid sequence of SEQ ID NO: 1 and which has choline acetyltransferase activity, an amino acid sequence having choline acetyltransferase activity and having sequence similarity of at least 80% to the amino acid sequence of SEQ ID NO: 1 may be preferably used, and an amino acid sequence having choline acetyltransferase activity and having sequence similarity of at least 85, 90 or 95% to the amino acid sequence of SEQ ID NO: 1 may be highly preferred.

A protein having an amino acid sequence shown in the group B can be prepared, for example, according to a method described later using a polynucleotide encoding an amino acid sequence shown in the group B.

An insect choline acetyltransferase can be used as a reagent that provides an indicator to evaluate pesticidal activity. Specifically, for example, an insect choline acetyltransferase can be used as a reagent that provides an indicator to evaluate pesticidal activity by using as a choline acetyltransferase used in the method of assaying a pesticidal ability using a choline acetyltransferase. In addition, a more specific method can be performed according to the aforementioned method of measuring the activity of a choline acetyltransferase.

In addition, when an insect choline acetyltransferase is used as a reagent that provides an indicator to evaluate a pesticidal activity, it is preferable that an insect choline acetyltransferase is a choline acetyltransferase having an amino acid sequence selected from the group B.

A polynucleotide having a nucleotide sequence encoding an amino acid sequence shown in the group B (hereinafter, referred to as polynucleotide group B in some cases) has a nucleotide sequence from which a protein having an amino acid sequence shown in the group B can be produced, in a cell of an organism or an in vitro translation system. A polynucleotide group B may be DNA cloned from a nature, DNA in which deletion, substitution or addition of a nucleotide is introduced into DNA cloned from a nature, for example, by a site-directed mutagenesis or a random mutagenesis, or an artificially synthesized DNA. Specifically, examples include a polynucleotide comprising the nucleotide sequence of SEQ ID NO: 2.

<First Obtaining Method>

For example, a method of obtaining a polynucleotide comprising the nucleotide sequence of SEQ ID NO: 3 will be shown below. The polynucleotide contains a polynucleotide comprising the nucleotide sequence of SEQ ID NO: 2 and is included in the polynucleotide group B. The method comprises obtaining total RNA from cotton aphids, synthesizing cDNA library from the RNA, and PCR amplification to obtain the polynucleotide of interest.

A population of adults and larvae of *Aphis gossypii*, which have been reared on leaves of potted cucumber, is scraped from the surface of the leaves with a small brush, and 630 mg of the obtained population is crushed into a powder in liquid nitrogen using a mortar and a pestle. From the resulting frozen crushed powder, RNA is isolated using a RNA extracting reagent ISOGEN (manufactured by Nippon Gene) as follows. After 10 ml of ISOGEN is added to the frozen crushed powder in the mortar, the crushed powder is ground for 10 minutes while kept on ice. After grinding, a fluid sample is transferred to a 15 ml tube with a pipette, and 2 ml of chloroform (manufactured by Wako Pure Chemical Industries, Ltd.) is added thereto. Immediately, the mixture is vigorously shaken for 15 seconds and then left at rest at room temperature for 3 minutes. Then, the resulting mixture is centrifuged at 12,000×g at 4° C. for 15 minutes, and each 5 ml of aqueous layer are transferred to two new tubes. After 5 ml of ISOGEN is added to each tube, the mixture was immediately shaken vigorously for 15 seconds, and left at rest at room temperature for 3 minutes. Then, the resulting mixture is centrifuged at 12,000×g at 4° C. for 15 minutes, and each 10 ml of aqueous layer are transferred to new 50 ml tubes, respectively. Subsequently, 10 ml of isopropanol (manufactured by Wako Pure Chemical Industries, Ltd.) is added to each tube, and the mixture is kept on ice for 30 minutes. The resulting mixture is centrifuged at 12,000×g at 4° C. for 10 minutes to precipitate RNA. After the supernatant is removed, 20 ml of 70% ethanol is added to the residue. The resulting mixture is centrifuged at 10,000×g at 4° C. for 5 minutes. After the supernatant is removed, the precipitate of total RNA is slightly dried and then dissolved in 1 ml of commercially available RNase-free water (Nacalai Tesque, Inc.). An absorbance of the prepared total RNA is measured at 260 nm to calculate a concentration according to a conventional method.

RT-PCR is performed employing total RNA of cotton aphid obtained by the aforementioned method as a template, and using random primers (manufactured by Invitrogen) and superscript III (manufactured by Invitrogen) according to the manual annexed to the reagent, to synthesized a first-strand cDNA.

PCR is performed employing cDNA library of cotton aphid obtained by the aforementioned method as a template, and using an oligonucleotide primer comprising the nucleotide sequence of SEQ ID NO: 4 and an oligonucleotide primer comprising the nucleotide sequence of SEQ ID NO: 5 as well as Pfu Ultra HF Taq polymerase (manufactured by Stratagene) according to the manual annexed to the reagent. The PCR conditions areas follows: an initial denaturation at 94° C. for 10 minutes; followed by 35 cycles of PCR, one cycle being 94° C. for 20 seconds, 53° C. for 20 seconds, and 72° C. for 3 minutes; followed by 72° C. for 7 minutes.

As described above, a polynucleotide comprising the nucleotide sequence of SEQ ID NO: 3 can be obtained.

<Second Obtaining Method>

A polynucleotide shown in the polynucleotide group B can be also obtained by preparing a polynucleotide with mutation introduced therein by a method utilizing amber mutation which is the aforementioned site-directed mutagenesis, a method by PCR using a primer for introducing mutation or the like, using as a template a polynucleotide comprising the nucleotide sequence of SEQ ID NO: 2 or 3.

<Third Obtaining Method>

A polynucleotide shown in the polynucleotide group B can be also obtained by a hybridization method using a polynucleotide comprising the nucleotide sequence of SEQ ID NO: 2 or 3 as a probe. More specifically, the third obtaining method can be performed according to the aforementioned conventional hybridization method described in Sambrook J., Frisch E. F., Maniatis T., Molecular Cloning 2nd edition, published by Cold Spring Harbor Laboratory press.

<Fourth Obtaining Method>

Alternatively, a polynucleotide shown in the polynucleotide group B can be also obtained by preparing a primer based on an amino acid sequence of the known insect choline acetyltransferase and performing PCR. For isolation of homologues of choline acetyltransferase gene from other insect species such as German cockroach (*Blatella germanica*), degenerate primers are designed using Codehop program (publicly accessible on the website of Blocks Protein Analysis Server operated within the Fred Hutchinson Cancer Research Center at blocks.fhcrc.org/blocks/codehop.html), and based on the sequence of the aforementioned cotton aphid choline acetyltransferase gene and the previously-known amino acid sequences from such as *D. melanogaster* (NCBI accession number P07668), *Ceanorhabditis elegans* (P32756) and *Anopheles gambiae* (XP_312586).

Partial sequences of a homologue of choline acetyltransferase gene of a selected insect species are amplified by a series of PCR using first-strand cDNA derived from the insect species as a template. Herein, the first-strand cDNA as a template is prepared by the aforementioned method using Superscript III. Amplification by PCR is performed using a set of degenerate primers as a forward primer and a reverse primer as well as Amplitaq Gold (manufactured by Applied Biosystems) according to the manufacturer's procedure annexed to the reagent. The PCR conditions are those for touchdown PCR as follows: an initial denaturation at 94° C. for 10 minutes; followed by 10 cycles of touchdown-PCR, one cycle being 94° C. for 30 seconds, 60° C. for 1 minute with a decrease of 1° C. per cycle, and 72° C. for 1 minute and 30 seconds; followed by 25 cycles of PCR, one cycle being 94° C. for 30 seconds, 50° C. for 1 minute, and 72° C. for 1 minute and 30 seconds; and followed by 72° C. for 7 minutes. The PCR product is analyzed and purified by agarose gel electrophoresis to obtain DNA of interest. Further, the obtained DNA is cloned into the pCR4-TOPO vector (manufactured by Invitrogen), and sequenced.

Then, primers specific for the resulting partial sequences of the insect homologue of choline acetyltransferase gene are designed, and 3' RACE PCR or 5' RACE PCR is performed in order to obtain a full-length sequence of the gene. The 3'RACE PCR is performed employing first-strand cDNA prepared from the insect total RNA as a template and using SMART PCR cDNA Synthesis Kit (manufactured by Clontech) according to the manufacturer's instructions annexed to the kit. The 5'RACE PCR is performed employing first-strand cDNA prepared from the insect total RNA as a template and using 5'/3' RACE Kit, $2^{nd}$ Generation (manufactured by Roche) according to the manufacturer's instructions annexed to the kit.

In 3' RACE reaction, a forward primer specific for the sequence of interest is used in combination with universal primer mix (UPM) contained in SMART PCR cDNA Synthesis Kit as a reverse primer. The PCR conditions are those for touchdown PCR as follows: an initial denaturation at 94° C. for 10 minutes; followed by 10 cycles of touchdown-PCR, one cycle being 94° C. for 20 seconds, 60° C. for 20 seconds with a decrease of 1° C. per cycle, and 72° C. for 2 minutes; followed by 25 cycles of PCR, one cycle being 94° C. for 20 seconds, 50° C. for 20 seconds, and 72° C. for 3 minutes; and followed by 72° C. for 7 minutes. The resulting PCR product is analyzed and purified by agarose gel electrophoresis to obtain DNA of interest. Further, the obtained DNA is cloned into the pCR4-TOPO vector (manufactured by Invitrogen), and sequenced.

When a distinct amplification product is not obtained by the first-round PCR, nested PCR is performed using the first-round PCR product as a template. As primers, a specific forward primer which is designed to bind to internal sequence of the first-round PCR product is used in combination with NUP primer contained in SMART PCR cDNA Synthesis Kit as a reverse primer. The PCR conditions are as follows: an initial denaturation at 95° C. for 10 minutes; followed by 35 cycles of PCR, one cycle being 95° C. for 20 seconds, 50° C. for 20 seconds, and 72° C. for 3 minutes; followed by 72° C. for 7 minutes. The resulting PCR product is analyzed and purified by agarose gel electrophoresis to obtain DNA of interest. Further, the obtained DNA is cloned into the pCR4-TOPO vector (manufactured by Invitrogen), and sequenced.

In 5' RACE reaction, a reverse primer specific for the sequence of interest is used in combination with Oligo-d(T)-anchor primer1 contained in 5'/3' RACE Kit, 2nd Generation as a forward primer. The PCR conditions are those for touchdown PCR as follows: an initial denaturation at 94° C. for 10 minutes; followed by 10 cycles of touchdown-PCR, one cycle being 94° C. for 30 seconds, 58° C. for 30 seconds with a decrease of 1° C. per cycle, and 72° C. for 2 minutes; followed by 25 cycles of PCR, one cycle being 94° C. for 30 seconds, 48° C. for 1 minute, and 72° C. for 2 minutes; and followed by 72° C. for 7 minutes. The resulting PCR product is analyzed and purified by agarose gel electrophoresis to obtain DNA of interest. Further, the obtained DNA is cloned into the pCR4-TOPO vector (manufactured by Invitrogen), and sequenced.

When a distinct amplification product is not obtained by the first-round PCR, nested PCR is performed using the first-round PCR product as a template. As primers, a specific reverse primer which is designed to bind to internal sequence of the first-round PCR product is used in combination with PCR Anchor primer contained in 5'/3'RACE Kit, 2nd Generation as a forward primer. The PCR conditions are as follows: an initial denaturation at 94° C. for 10 minutes; followed by 10 cycles of PCR, one cycle being 94° C. for 15 seconds, 55° C. for 30 seconds, and 72° C. for 40 seconds; followed by 25 cycles of PCR, one cycle being 94° C. for 15 seconds, 55° C. for 30 seconds, and 72° C. for 40 seconds extended with 20 seconds each cycle; followed by 72° C. for 7 minutes. The resulting PCR product is analyzed and purified by agarose gel electrophoresis to obtain DNA of interest. Further, the obtained DNA is cloned into the pCR4-TOPO vector (manufactured by Invitrogen), and sequenced.

The above sequencing results reveal 5'-terminal sequence and 3'-terminal sequence, each encoding N-terminal region and C-terminal region of the insect choline acetyltransferase, respectively.

Thus, a polynucleotide shown in the polynucleotide group B can be obtained by PCR by preparing primers based on amino acid sequences of the known insect choline acetyltransferases.

A polynucleotide comprising a nucleotide sequence complementary to a nucleotide sequence of the polynucleotide group B can be used for obtaining a polynucleotide shown in the polynucleotide group B using a hybridization method.

The obtaining method in the present invention comprises a step of detecting a desired polynucleotide by hybridization, a step of identifying the detected desired polynucleotide, and a step of recovering the identified desired polynucleotide. Each step will be explained specifically below.

A step of detecting a desired polynucleotide by hybridization, and a step of identifying the detected desired polynucleotide can be performed by using, as a probe, a polynucleotide having a nucleotide sequence having complementarity to a nucleotide sequence of a polynucleotide group B, according to the method described, for example, in "Molecular Cloning: A Laboratory Manual 2nd edition" (1989), Cold Spring Harbor Laboratory Press, "Current Protocols In Molecular Biology" (1987), John Wiley & Sons, Inc. ISBN0-471-50338-X and the like.

Specifically, for example, a DNA comprising a nucleotide sequence complementary to the nucleotide sequence of SEQ ID NO: 2 is labeled with a radioisotope or a fluorescently labeled by the known method using Random Primed DNA Labelling Kit (manufactured by Boehringer), Random Primer DNA Labelling Kit Ver. 2 (manufactured by TAKARA SHUZO Co., Ltd.), ECL Direct Nucleic Acid Labelling and Ditection System (manufactured by Amersham Biosciences), or Megaprime DNA-labelling system (manufactured by Amersham Biosciences), and this can be used as probe.

Examples of condition for hybridization include stringent condition, and specifically, examples include condition under which incubation is performed at 65° C. in the presence of 6×SSC (0.9M NaCl, 0.09M sodium citrate), a 5× Denhart's solution (0.1% (w/v) Ficoll 400, 0.1% (w/v) polyvinylpyrrolidone, 0.1% BSA), 0.5% (w/v) SDS and 100 µg/ml denatured salmon spermatozoon DNA, or in a DIG EASY Hby solution (Boehringer Mamnnheim) containing 100 µg/ml denatured salmon spermatozoon DNA, then, incubation is performed two times at room temperature for 15 minutes in the presence of 1×SSC (0.15 m NaCl, 0.015 m sodium citrate) and 0.5% SDS and, further, incubation is performed at 68° C. for 30 minutes in the presence of 0.1×SSC (0.015 m NaCl, 0.0015 m sodium citrate) and 0.5% SDS.

More specifically, for example, a probe labeled with $^{32}$P can be made by employing a polynucleotide comprising a nucleotide sequence complementary to a nucleotide sequence of a polynucleotide group B as a template, using Megaprime DNA-labelling system (manufactured by Amersham Pharmacia Biotech) and using a reaction solution designated in a kit. Colony hybridization is performed using this probe according to a conventional method, incubation is performed at 65° C. in the presence of 6×SSC (0.9M NaCl, 0.09M sodium citrate), a 5× Denhart's solution (0.1% (w/v) Ficoll 400, 0.1% (w/v) polyvinylpyrrolidone, 0.1% BSA), 0.5% (w/v) SDS and 100 µg/ml denatured salmon spermatozoon DNA, or in a DIG EASY Hyb solution (Boehringer Mannheim) containing 100 µg/ml denatured salmon spermatozoon DNA, then, incubation is performed two times at room temperature for 15 minutes in the presence of 1×SSC (0.15 m NaCl, 0.015 m sodium citrate) and 0.5% SDS and, further, incubation is performed at 68° C. for 30 minutes in the presence of 0.1×SSC (0.015 m NaCl, 0.0015 m sodium citrate) and 0.5% SDS, thereby, (a colony containing) a hybridizing polynucleotide can be detected. Thus, a desired polynucleotide can be detected by hybridization, and the detected desired polynucleotide can be identified.

For recovering the identified desired polynucleotide, a plasmid DNA can be recovered from a colony containing the polynucleotide detected and identified by the aforementioned method, for example, according to a method such as the alkali method described in "Molecular Cloning: A Laboratory Manual 2nd edition" (1989), Cold Spring Harbor Laboratory Press. A nucleotide sequence of the recovered desired polynucleotide (plasmid DNA) can be confirmed by a Maxam Gilbert method (described, for example, in Maxam, A. M and W. Gilbert, Proc. Natl. Acad. Sci. USA, 74, 560, 1977 etc.) or a Sanger method (described, for example, in Sanger, F. and A. R. Coulson, J. Mol. Biol., 94, 441, 1975, Sanger, F, and Nicklen and A. R. Coulson., Proc. Natl. Acad. Sci. USA, 74, 5463, 1977 etc.). Thereupon, for example, commercially available Termo Seqenase II dye terminator cycle sequencing kit (manufactured by Amersham biosciences), Dye Terminator Cycle Sequencing FS Ready Reaction Kit (manufactured by Applied Biosystems) and the like can be used.

A polynucleotide comprising a partial nucleotide sequence of a nucleotide sequence of the polynucleotide group B or a nucleotide sequence complementary to the partial nucleotide sequence can be used for obtaining a polynucleotide shown in the polynucleotide group B using PCR. More specifically, examples include a polynucleotide comprising a nucleotide sequence of SEQ ID NO: 4 or 5. The obtaining method in the present invention includes a step of amplifying a desired polynucleotide by PCR, a step of identifying the amplified desired polynucleotide, and a step of recovering the identified desired polynucleotide. Each step will be specifically explained below.

In a step of amplifying a desired polynucleotide by PCR, specifically, a DNA designed and synthesized from a partial nucleotide sequence of a nucleotide sequence of a polynucleotide group B or a nucleotide sequence complementary to the partial nucleotide sequence, based on an about 20 bp to about 40 bp nucleotide sequence, for example, a nucleotide sequence selected from a nucleotide sequence of SEQ ID NO: 2 and a sequence complementary to the nucleotide sequence of SEQ ID NO: 2 can be used as a primer set. Examples of a primer set include a set of a polynucleotide comprising a nucleotide sequence represented by SEQ ID NO: 4 and a polynucleotide comprising the nucleotide sequence of SEQ ID NO: 5. A PCR reaction solution is prepared, for example, by adding a reaction solution designated by a commercially available PCR kit to a cDNA library prepared by the aforementioned method. Reaction condition can be changed depending on a primer set to be used, and for example, condition under which after incubation at 94° C. for 10 seconds, around 40 cycles is repeated, 1 cycle being 94° C. for 15 seconds, 60° C. for 15 seconds, and 72° C. for 3 minutes and, further, incubation is performed at 72° C. for 3 minutes, condition under which incubation is performed at 94° C. for 2 minutes, thereafter, incubation is performed at about 8° C. for 3 minutes and, thereafter, around 40 cycles is repeated, 1 cycle being 94° C. for 30 seconds, 55° C. for 30 seconds, and 72° C. for 4 minutes, or condition under which 5 to 10 cycles is performed, 1 cycle being incubation at 94° C. for seconds and, then, 72° C. for 4 minutes and, further, around 20 to 40 cycles is performed, 1 cycle being incubation at 94° C. for 5 seconds and, then, 70° C. for 4 minutes, can be used. In the PCR, for example, PfuUltra High Fidelity polymerase (manufactured by Stratagene), Amplitaq Gold (manufactured by Applied Biosystems), Takara Heraculase (Trademark) (manufactured by TAKARA SHUZO Co., Ltd.), a DNA polymerase contained in Advantage cDNA PCR Kit (manufactured by Clonetech), TaKaRa Ex Taq (manufactured by TAKARA SHUZO Co., Ltd.), PLATINUM™ PCR SUPER Mix (manufactured by Lifetech Oriental) can be used.

Identification of a desired polynucleotide amplified by PCR can be performed by measuring a molecular weight by agarose gel electrophoresis according to the method described in "Molecular Cloning: A Laboratory Manual 2nd edition" (1989), Cold Spring Harbor Laboratory Press. In addition, regarding the amplified desired polynucleotide, a sequencing reaction is performed using a commercially available DNA sequencing reaction kit, for example, Dye Terminator Cycle Sequencing FS Ready Reaction Kit (manufactured by Applied Biosystems) according to a manual annexed to the kit, and the nucleotide is analyzed using a DNA sequencer 3100 (manufactured by Applied Biosystems), thereby, a nucleotide sequence of the amplification fragment can be read.

Examples of a method of recovering the identified desired polynucleotide include a method of purifying and recovering the aforementioned polynucleotide identified by agarose gel electrophoresis from an agarose gel according to the method described in "Molecular Cloning: A Laboratory Manual 2nd edition" (1989), Cold Spring Harbor Laboratory Press. In addition, the thus recovered polynucleotide or a desired polynucleotide amplified by PCR can be cloned into a vector according to a conventional method described in "Molecular Cloning: A Laboratory Manual 2nd edition" (1989), Cold Spring Harbor Laboratory Press, and "Current Protocols In Molecular Biology" (1987), John Wiley & Sons, Inc. ISBN0-471-50338-X. Examples of a vector to be used include pUCA119 (manufactured by TAKARA SHUZO Co., Ltd.), pTVA118N (manufactured by TAKARA SHUZO Co., Ltd.), pBluescriptII (manufactured by Toyobo Co., Ltd.), pCR2.1-TOPO (manufactured by Invitrogen) and the like. In addition, a nucleotide sequence of the cloned polynucleotide can be confirmed by a Maxam Gilbert method (described, for example, in Maxam, A. M & W. Gilbert, Proc. Natl. Acad. Sci. USA, 74, 560, 1977) or a Sanger method (described, for example, in Sanger, F. & A. R. Coulson, J. Mol. Biol., 94, 441, 1975, Sanger, F, & Nicklen and A. R. Coulson., Proc. Natl. Acad. Sci. USA, 74, 5463, 1977). Thereupon, for example, a commercially available Termo Seqenase II dye terminator cycle sequencing kit (manufactured by Amersham biosciences), Dye Terminator Cycle Sequencing FS Ready Reaction Kit (manufactured by Applied Biosystems) and the like can be used.

In addition, a polynucleotide having a partial nucleotide sequence of a nucleotide sequence of the polynucleotide group B or a nucleotide sequence complementary to the partial nucleotide sequence can be used for obtaining a polynucleotide shown in the polynucleotide group B using not only a PCR method, but also the aforementioned hybridization method. More specifically, examples include a polynucleotide comprising a nucleotide sequence represented by SEQ ID NO: 4 or 5.

Examples of a method for preparing a protein comprising an amino acid sequence shown in the group B include a method of culturing a transformant with a polynucleotide selected from a polynucleotide group B introduced therein, and recovering the produced protein. In addition, for preparing a transformant used herein, it is a work such as preparation of a circular polynucleotide containing a polynucleotide in which a polynucleotide selected from a polynucleotide group B is operably ligated to a bacteriophage promoter. The method will be explained in detail below.

In addition, a choline acetyltransferase shown in the group A which is used in the method of assaying a pesticidal activity using a choline acetyltransferase can be prepared and obtained by the similar method, using a polynucleotide comprising a nucleotide sequence encoding the choline acetyltransferase.

A bacteriophage promoter means a promoter of a gene contained in a bacteriophage genome. Among them, examples of a promoter of bacteriophage used for expressing a foreign gene include a promoter of T7 RNA polymerase gene, T3 RNA polymerase gene and SP6 RNA polymerase gene.

In the present invention, "operably linked" means that a polynucleotide containing a gene of interest is linked downstream of a polynucleotide containing a promoter sequence so that the gene of interest can be transcribed in a used transcription system. Specifically, for example, when a promoter of T7 RNA polymerase gene described later is used, a polynucleotide containing a gene of interest may be linked downstream of a promoter of T7 RNA polymerase gene. In addition, for example, when a promoter other than T7 RNA polymerase gene promoter is used, it is also possible to link a polynucleotide containing a gene of interest downstream of a polynucleotide containing a promoter sequence other than T7 RNA polymerase gene promoter. More specifically, for example, when a plasmid pET41a(+) (Novagen) vector utilizing T7 RNA polymerase gene promoter is used, the polynucleotide can be operably linked by ligating a gene of interest into a restriction enzyme site such as NcoI, EcoRV, BamHI, EcoRI, StuI, PstI, SacI, SaiI, HindIII, NotI, EagI and XhoI located downstream of T7 RNA polymerase gene promoter.

In the present invention, the "circular polynucleotide" is a polynucleotide which has been made to be circular by binding of ends of the polynucleotide strand, and examples include chromosomal DNAs of many bacteria in addition to a plasmid DNA, a bacmid DNA and the like.

A plasmid DNA is a relatively low-molecular circular polynucleotide, and examples include pET (manufactured by Takara Mirus Bio Inc.) and pBluescriptII (manufactured by Stratagene), used for cloning and expression in *E. coli*. Additional examples include pFastBac1, pFastBac HT A, pFastBac HT B, pFastBac HT C, pFastBac Dual, pBlueBacII (manufactured by Invitrogen), pAcSG2 (manufactured by Pharmingen) and the like, which contain a baculovirus expression cassette.

The bacmid is a high molecular weight DNA that consists of a BAC (bacterial artificial chromosome) that contains the entire baculoviral genome, for example bMON14272 (136 kb) that is present in DH10Bac™ *E. coli* cells (invitrogen). Bacmid DNA propagates as a large plasmid in *E. coli* cells and may contain an expression cassette for expression of a foreign gene under control of a baculoviral promoter.

A circular polynucleotide in which a polynucleotide comprising a nucleotide sequence encoding an amino acid sequence shown in the group B is operably linked to a bacteriophage promoter is specifically, for example, a circular polynucleotide containing a DNA comprising a cotton aphid choline acetyltransferase gene operably linked to a bacteriophage T7 RNA polymerase promoter, and can be prepared and obtained, for example, according to the following method.

DNA fragment containing the choline acetyltransferase gene is amplified by PCR, using a plasmid DNA containing a cotton aphid choline acetyltransferase gene cloned in accordance with the aforementioned method as a template, with a primer specific to the choline acetyltransferase gene to which a Bam HI restriction site is added and a primer specific to the choline acetyltransferase gene to which a XhoI restriction site is added. The resulting PCR products are cleaved with Bam HI and XhoI, and the obtained approximately 2.2 kbp of DNA fragment containing the cotton *aphis* choline acetyltransferase gene is ligated to a plasmid vector pET41a(+) (manufactured by Novagen) digested in advance with Bam HI and XhoI. The plasmid obtained in this way is one example of circular polynucleotide containing DNA fragment comprising the cotton *aphis* choline acetyltransferase gene operably linked to bacteriophage T7 RNA polymerase promoter.

Similarly, a circular polynucleotide can be prepared by ligating nucleotides encoding an amino acid sequence shown in the group B to a vector.

In the present invention, the "origin of replication" is the specific DNA sequence necessary for replicating itself in a host cell. Examples of origin of replication include colE1 and f1 for bacterial plasmids.

A transformant is a eukaryotic cell or a prokaryotic cell which has been genetically altered by introduction of a foreign polynucleotide into a cell. Examples of a transformant include an *Escherichia coli* cell transformed by introduction of a plasmid used for gene cloning or gene expression in *E. coli*, such as pET (Novagen) or pBluescript II (Stratagene). In addition, examples of the technique of introducing a DNA into a host cell include transformation, transfection, protoplast fusion, lipofection, electroporation and the like.

Examples of a transformant in which a polynucleotide encoding an amino acid sequence shown in the group B is introduced include transformed *Escherichia coli* in which a DNA comprising a cotton aphid choline acetyltransferase gene operably linked to a bacteriophage T7 RNA polymerase promoter is introduced. Specifically, the transformant can be prepared according to the following method.

A transformant can be prepared by introducing into an *Escherichia coli* cell a plasmid vector pET41a(+) (Novagen) in which a DNA containing a cotton aphid choline acetyltransferase gene is inserted between Bam HI site and Xho I site, according to the method described in "Molecular Cloning: A Laboratory Manual 2nd edition" (1989), Cold Spring Harbor Laboratory Press. Alternatively, a transformant can be also prepared by transforming *E. coli* using the aforementioned plasmid DNA into which a fragment containing a bacteriophage T7 RNA polymerase promoter and a cotton aphid choline acetyltransferase gene is inserted, according to a method described in a manual annexed to *Escherichia coli* BL21(DE3) competent cells (Invitrogen).

A choline acetyltransferase can be prepared by culturing a transformant prepared by the aforementioned method, and recovering the produced insect-derived choline acetyltransferase.

Choline acetyltransferase protein may be produced by a recombinant *E. coli* expression system. This system is the most frequently used prokaryotic expression system for the high-level production of heterologous proteins. *E. coli* is genetically and physiological the best characterized organism known, it is easy to manipulate, many tools are available, it is able to grow very fast, it grows on cheap complex or well-defined minimal media and it has an extremely high capacity to synthetize heterologous protein.

Alternatively, choline acetyltransferase protein may be produced by for example a recombinant baculovirus/Sf9 cell expression system. This system is one of the most powerful and versatile eukaryotic expression systems available, and may be used to express heterologous genes from many different sources, including fungi, plants, bacteria and viruses.

In addition, an insect-derived choline acetyltransferase produced by culturing a transformant is lysed by a method such as sonication, French press, and Dyno mill, and recovered in a form contained in a cell crude extract, and a purified protein can be obtained by using a procedure conventionally used in enzyme purification such as ion exchange column chromatography, reverse phase column chromatography, gel filtration column chromatography and the like. Alternatively, when it is devised that an insect-derived choline acetyltransferase is produced in a form with His-tag, a purified protein can be obtained rapidly from a cell crude extract by affinity column chromatography which specifically recognizes and binds to the His-tag. By the method, an insect-derived choline acetyltransferase can be prepared.

For example, an insect-derived choline acetyltransferase can be prepared by culturing a *E. coli* cell transformed with a DNA fragment containing a cotton aphid choline acetyltransferase gene operably linked to bacteriophage T7 RNA polymerase promoter, and grinding the cell with a French press, followed by purification with column chromatography.

To be more concrete, for example, a recombinant *E. coli* containing the DNA fragment comprising the cotton aphid choline acetyltransferase gene operably linked to the bacteriophage T7 RNA polymerase promoter, which prepared by the above method, is rotary cultured overnight at 37° C., 250 rpm. In the next morning, the culture is diluted 1/100 in LB medium containing 50 mg/L of Kanamycin, to which IPTG is added until a final concentration of 10 μM, and grown at 22° C., 60 rpm for 4 days to produce recombinant choline acetyltransferase protein in the *E. coli*. The culture is centrifuged at 7,000 rpm for 10 minutes to collect the *E. coli*. To the collected *E. coli*, breaking buffer (0.1M Sodium phosphate buffer pH 7.6, 1 tablet of Complete EDTA-free protease inhibitor cocktail (manufactured by Roch)) is added and suspended. Further, the *E. coli* is lysed with a pressure between 1,300 psi and 1,500 psi, using French press (manufactured by Thermo Spectronic), in accordance with the method described in the attached instruction. The French pressed solution is centrifuged at 14,000 rpm, 2° C., for 60 minutes, and the resulting supernatant is filtrated through a 0.45 μm filter. The sample is injected into HiTrap Chelating HP (manufactured by Amersham biosciences) column or HisTrap HP (manufactured by Amersham biosciences) column, which is equilibrated with His buffer A (0.1M Sodium phosphate buffer pH 7.6, 10% glycerol). Afterwards, the column is washed with 5 column volumes of a buffer, in which 95% of His buffer A and 5% of His buffer B (0.1M Sodium phosphate buffer pH 7.6, 500 mM imidazole, 10% glycerol) are mixed. Next, the column is washed with 15 column volumes of a buffer, in which 90% of His buffer A and 10% of His buffer B are mixed. Next, the column is washed with 15 column volumes of a buffer, in which 85% of His buffer A and 15% of His buffer B are mixed. Next, the column is washed with 15 column volumes of a buffer, in which 80% of His buffer A and 20% of His buffer B are mixed. Afterwards, 15 column volumes of a buffer in which 60% of His buffer A and 40% of His buffer B are mixed is prepared and injected into the column. One ml of aliquots of the eluted fraction is pooled and an aliquot is analyzed with SDS-PAGE to determine fractions containing 115 kDa of choline acetyltransferase. These fractions are the solution enriched in the target choline acetyltransferase.

An insect choline acetyltransferase comprising an amino acid sequence shown in the group B can be used as a research tool. For example, it can be used as a research tool for performing study such as assaying of the pestcidal ability, screening of a chemical substance having a pestcidal ability, and the like. In addition, for example, also in study of analyzing action and mechanism of an agent which acts on a choline acetyltransferase, a choline acetyltransferase can be utilized as a research tool.

In addition, polynucleotides encoding amino acid sequences shown in the group B and polynucleotides having a nucleotide sequence having complementarity to them, as well as partial nucleotide sequences of polynucleotides encoding amino acid sequences shown in the group B, or polynucleotides having nucleotide sequences having complementarity to the partial nucleotide sequences, and a polynucleotide complying a nucleotide sequence represented by SEQ ID NO: 4 or 5 can be used as a research tool. For example, a part of them functions as a polynucleotide used in a method of preparing a choline acetyltransferase as described above. In addition, apart can be used as an important research tool for performing obtaining a polynucleotide shown in a polynucleotide group B using PCR, or obtaining a polynucleotide shown in a polynucleotide group B using hybridization, as described above.

Particularly, upon implementation of screening of a pestcidal agent, they can be used as an experimental tool for an experiment which is performed for screening. Specifically, they can be used as an experimental tool for an experiment which is performed upon implementation of the assaying of a pestcidal ability, screening of a chemical substance having a pestcidal ability, and the like.

Further, the present invention also includes a system which comprises a means to input, store and manage data information of an ability of test substances, wherein said ability is an ability to modulate the activity of an insect choline acetyltransferase (hereinafter, referred to as means a in some cases), a means to query and retrieve the data information based on a desired criterion (hereinafter, referred to as means b in some cases), and a means to display and output the result which is queried and retrieved (hereinafter, referred to as means c in some cases) (hereinafter, referred to as present system in some cases).

First, a means a will be explained. A means a is a means to, after data information of an ability to modulate the activity of an insect-derived choline acetyltransferase possessed by the test substance is inputted, store and manage the inputted information, as described above. The information is inputted by an inputting means 1, and is usually memorized in a memory means 2. Examples of an inputting means include means which can input the information such as a keyboard and a mouse. When inputting and storing•managing of the information are completed, a procedure progresses to a next means b. For storing•managing the information, a large amount of data may be effectively stored and managed by inputting information having a data structure using a hardware such as a computer, and a software such as OS and database management, and storing the information into a suitable memory device, for example, computer-readable recording medium such as a flexible disc, a photomagnetic disc, CD-ROM, DVD-ROM, and a hard disc.

A means b will be explained. A means b is a means to query and retrieve the data information stored and managed by a means of a based on criterion for obtaining a desired result, as described above. For the information, when criterion for querying and retrieving is inputted by an inputting means 1, and information in conformity with the criterion is selected among the information usually memorized in a memory means 2, a procedure progresses to a next means c. The selected result is usually memorized in a memory means 2 and, further, can be displayed by a displaying•outputting means 3.

A means c will be explained. A means c is a means to display and output the result which is queried and retrieved, as described above. Examples of the displaying•outputting means 3 include a display, a printer and the like, and the result may be displayed on a display device of a computer, or may be outputted on a paper by printing.

EXAMPLES

The present invention will be explained in more detail below by way of Examples, but the present invention is not limited to these particular Examples.

Example 1

Extraction of Total RNA from Cotton Aphid and German Cockroach (1) Extraction of Total RNA from Cotton Aphid.

A population of adults and larvae of cotton aphid (*Aphis gossypii*), which had been reared on leaves of potted cucumber, was scraped from the surface of the leaves with a small brush, and 630 mg of the obtained population was crushed into a powder in liquid nitrogen using a mortar and a pestle. From the resulting frozen crushed powder, RNA was isolated using a RNA extracting reagent ISOGEN (manufactured by Nippon Gene) as follows. After 10 ml of ISOGEN was added to the frozen crushed powder in the mortar, the crushed powder was ground for 10 minutes while kept on ice. After grinding, a fluid sample was transferred to a 15 ml tube with a pipette, and 2 ml of chloroform (manufactured by Wako Pure Chemical Industries, Ltd.) was added thereto. Immediately, the mixture was vigorously shaken for 15 seconds and then left at rest at room temperature for 3 minutes. Then, the resulting mixture was centrifuged at 12,000×g at 4° C. for 15 minutes, and each 5 ml of aqueous layer were transferred to two new tubes. After 5 ml of ISOGEN was added to each tube, the mixture was immediately shaken vigorously for 15 seconds, and left at rest at room temperature for 3 minutes. Then, the resulting mixture was centrifuged at 12,000×g at 4° C. for 15 minutes, and each 10 ml of aqueous layer were transferred to new 50 ml tubes, respectively. Subsequently, 10 ml of isopropanol (manufactured by Wako Pure Chemical Industries, Ltd.) was added to each tube, and the mixture was kept on ice for 30 minutes. The resulting mixture was centrifuged at 12,000×g at 4° C. for 10 minutes to precipitate RNA. After the supernatant was removed, 20 ml of 70% ethanol was added to the residue. The resulting mixture was centrifuged at 10,000×g at 4° C. for 5 minutes. After the supernatant was removed, the precipitate of total RNA was slightly dried and then dissolved in 1 ml of commercially available RNase-free water (Nacalai Tesque, Inc.). A concentration of the prepared total RNA (calculated from an absorbance at 260 nm) was 6.9 mg/ml.

(2) Extraction of Total RNA from German Cockroach

Adults, nymphs and oothecae of artificially-reared German cockroach (*Blattella germanica*) were provided as samples. Ten (10) of adult males and 10 of adult females (individuals from each of which ootheca has been removed) were used as an adult sample of 1.1 g, 10 of nymph males and 10 of nymph females were used as a nymph sample of 1.0 g, and 26 oothecae were used as an ootheca sample of 1.0 g. Three kinds of these samples were separately crushed into a powder in liquid nitrogen using separate mortars and pestles. From each of the resulting frozen crushed powders, RNA was isolated using a RNA extracting reagent ISOGEN (manufactured by Nippon Gene) as follows. After 10 ml of ISOGEN was added to the frozen crushed powder in the mortar, the crushed powder was ground for 10 minutes while kept on ice. After grinding, a fluid sample was transferred to a 15 ml tube with a pipette, and 2 ml of chloroform (manufactured by Wako Pure Chemical Industries, Ltd.) was added thereto. Immediately, the mixture was vigorously shaken for 15 seconds and then left at rest at room temperature for 3 minutes. Then, the resulting mixture was centrifuged at 12,000×g at 4° C. for 15 minutes, and each 5 ml of aqueous layer were transferred to two new tubes. After 5 ml of ISOGEN was added to each tube, the mixture was immediately shaken vigorously for 15 seconds, and left at rest at room temperature for 3 minutes. Then, the resulting mixture was centrifuged at 12,000×g at 4° C. for 15 minutes, and each 10 ml of aqueous layer were transferred to new 50 ml tubes, respectively. Subsequently, 10 ml of isopropanol (manufactured by Wako Pure Chemical Industries, Ltd.) was added to each tube, and the mixture was kept on ice for 30 minutes. The resulting mixture was centrifuged at 12,000×g at 4° C. for 10 minutes to precipitate RNA. After the supernatant was removed, 20 ml of 70% ethanol was added to the residue. The resulting mixture was centrifuged at 10,000×g at 4° C. for 5 minutes. After the supernatant was removed, the precipitate of total RNA was slightly dried and then dissolved in 1 ml of commercially available RNase-free water (Nacalai Tesque, Inc.). A concentration of the prepared total RNA (calculated from absorbance at 260 nm) was 1.1 mg/ml in the case of adult-derived total RNA, was 2.5 mg/ml in the case of nymph-derived total RNA, and 1.4 mg/ml in the case of ootheca-derived total RNA.

Example 2

Isolation of Cotton Aphid Choline Acetyltransferase Gene

First-strand cDNA was prepared using total RNA from cotton aphid, random Primers (Invitrogen) and Superscript III (Invitrogen) for RT-PCR according to the manufacturer's procedure of Superscript III.

A full-length cDNA of cotton aphid choline acetyltransferase was amplified by PCR using an oligonucleotide comprising the nucleotide sequence of SEQ ID NO: 4 and an oligonucleotide comprising the nucleotide sequence of SEQ ID NO: 5, which are primers specific for the gene, and Pfu Ultra HF Taq polymerase (manufactured by Stratagene) according to the manufacturer's procedure. First-strand cDNA, prepared as described above, was used as template. The PCR conditions are as follows: an initial denaturation at 94° C. for 5 minutes; followed by 35 cycles of PCR, one cycle being 94° C. for 20 seconds, 53° C. for 20 seconds, and 72° C. for 3 minutes; followed by 72° C. for 10 minutes. The resulting PCR products were analyzed and purified by agarose gel electrophoresis to obtain DNA of interest. Further, the obtained DNA was cloned into the pCR4-TOPO vector (manufactured by Invitrogen), and sequenced to determine the nucleotide sequence of 2360 bp shown in SEQ ID NO: 3. Based on the sequence, an ORF encoding a cotton aphid choline acetyltransferase was identified as having the nucleotide sequence of 2211 bp shown in SEQ ID NO: 2. An amino acid sequence presumed from the nucleotide sequence of SEQ ID NO: 3 was the amino acid sequence of SEQ ID NO: 1.

Example 3

Isolation of German Cockroach Choline Acetyltransferase Gene

For isolation of homologues of choline acetyltransferase gene from other insect species such as German cockroach (*Blatella germanica*), degenerate primers are designed using Codehop program (publicly accessible on the website of Blocks Protein Analysis Server operated within the Fred Hutchinson Cancer Research Center at blocks.fhcrc.org/blocks/codehop.html), and based on the amino acid sequence of the aforementioned cotton aphid choline acetyltransferase and the previously-known amino acid sequences from such as *D. melanogaster* (NCBI accession number P07668), *Ceanorhabditis elegans* (P32756) and *Anopheles gambiae* (XP_312586).

Partial sequences of a homologue of choline acetyltransferase gene of a selected insect species are amplified by a series of PCR using first-strand cDNA derived from the insect species as a template. Herein, the first-strand cDNA as a template is prepared by the aforementioned method using Superscript III. Amplification by PCR is performed using a set of degenerate primers as a forward primer and a reverse primer as well as Amplitaq Gold (manufactured by Applied Biosystems) according to the manufacturer's procedure annexed to the reagent. The PCR conditions are those for touchdown PCR as follows: an initial denaturation at 94° C. for 10 minutes; followed by 10 cycles of touchdown-PCR, one cycle being 94° C. for 30 seconds, 60° C. for 1 minute with a decrease of 1° C. per cycle, and 72° C. for 1 minute and 30 seconds; followed by 25 cycles of PCR, one cycle being 94° C. for 30 seconds, 50° C. for 1 minute, and 72° C. for 1 minute and 30 seconds; and followed by 72° C. for 7 minutes. The PCR product is analyzed and purified by agarose gel electrophoresis to obtain DNA of interest. Further, the obtained DNA is cloned into the pCR4-TOPO vector (manufactured by Invitrogen), and sequenced.

Thus, partial sequence of a choline acetyltransferase gene of *Blatella germanica* is obtained.

Then, primers specific for the resulting partial sequences of the insect homologue of choline acetyltransferase gene are designed, and 3' RACE PCR or 5' RACE PCR is performed in order to obtain a full-length sequence of the gene. The 3'RACE PCR is performed employing first-strand cDNA prepared from the insect total RNA as a template and using SMART PCR cDNA Synthesis Kit (manufactured by Clontech) according to the manufacturer's instructions annexed to the kit. The 5'RACE PCR is performed employing first-strand cDNA prepared from the insect total RNA as a template and using 5'/3' RACE Kit, $2^{nd}$ Generation (manufactured by Roche) according to the manufacturer's instructions annexed to the kit.

In 3' RACE reaction, a forward primer specific for the sequence of interest is used in combination with universal primer mix (UPM) contained in SMART PCR cDNA Synthesis Kit as a reverse primer. The PCR conditions are those for touchdown PCR as follows: an initial denaturation at 94° C. for 10 minutes; followed by 10 cycles of touchdown-PCR, one cycle being 94° C. for 20 seconds, 60° C. for 20 seconds with a decrease of 1° C. per cycle, and 72° C. for 2 minutes; followed by 25 cycles of PCR, one cycle being 94° C. for 20 seconds, 50° C. for 20 seconds, and 72° C. for 3 minutes; and followed by 72° C. for 7 minutes. The resulting PCR product is analyzed and purified by agarose gel electrophoresis to obtain DNA of interest. Further, the obtained DNA is cloned into the pCR4-TOPO vector (manufactured by Invitrogen), and sequenced.

When a distinct amplification product is not obtained by the first-round PCR, nested PCR is performed using the first-round PCR product as a template. As primers, a specific forward primer which is designed to bind to internal sequence of the first-round PCR product is used in combination with NUP primer contained in SMART PCR cDNA Synthesis Kit as a reverse primer. The PCR conditions are as follows: an initial denaturation at 95° C. for 10 minutes; followed by 35 cycles of PCR, one cycle being 95° C. for 20 seconds, 50° C. for 20 seconds, and 72° C. for 3 minutes; followed by 72° C. for 7 minutes. The resulting PCR product is analyzed and purified by agarose gel electrophoresis to obtain DNA of interest. Further, the obtained DNA is cloned into the pCR4-TOPO vector (manufactured by Invitrogen), and sequenced.

In 5' RACE reaction, a reverse primer specific for the sequence of interest is used in combination with Oligo-d(T)-anchor primer1 contained in 5'/3' RACE Kit, 2nd Generation as a forward primer. The PCR conditions are those for touchdown PCR as follows: an initial denaturation at 94° C. for 10 minutes; followed by 10 cycles of touchdown-PCR, one cycle being 94° C. for 30 seconds, 58° C. for 30 seconds with a decrease of 1° C. per cycle, and 72° C. for 2 minutes; followed by 25 cycles of PCR, one cycle being 94° C. for 30 seconds, 48° C. for 1 minute, and 72° C. for 2 minutes; and followed by 72° C. for 7 minutes. The resulting PCR product is analyzed and purified by agarose gel electrophoresis to obtain DNA of interest. Further, the obtained DNA is cloned into the pCR4-TOPO vector (manufactured by Invitrogen), and sequenced.

When a distinct amplification product is not obtained by the first-round PCR, nested PCR is performed using the first-round PCR product as a template. As primers, a specific reverse primer which is designed to bind to internal sequence of the first-round PCR product is used in combination with PCR Anchor primer contained in 5'/3'RACE Kit, 2nd Generation as a forward primer. The PCR conditions are as follows: an initial denaturation at 94° C. for 10 minutes; followed by 10 cycles of PCR, one cycle being 94° C. for 15 seconds, 55° C. for 30 seconds, and 72° C. for 40 seconds; followed by 25 cycles of PCR, one cycle being 94° C. for 15 seconds, 55° C. for 30 seconds, and 72° C. for 40 seconds extended with 20 seconds each cycle; followed by 72° C. for 7 minutes. The resulting PCR product is analyzed and purified by agarose gel electrophoresis to obtain DNA of interest. Further, the obtained DNA is cloned into the pCR4-TOPO vector (manufactured by Invitrogen), and sequenced.

The above sequencing results reveal 5'-terminal sequence and 3'-terminal sequence, each encoding N-terminal region and C-terminal region of the insect choline acetyltransferase, respectively.

Example 4

Construction of Recombinant Plasmid

A choline acetyltransferase gene fragment to be cloned into a vector for expression in $E.$ $coli$ was amplified by PCR using an oligonucleotide comprising the nucleotide sequence of SEQ ID NO: 4 and an oligonucleotide comprising the nucleotide sequence of SEQ ID NO: 5, which are primers specific for the gene, and Pfu Ultra HF Taq polymerase (manufactured by Stratagene) according to the manufacturer's procedure. The cDNA obtained in Example 2 was used as template. The PCR conditions used were as follows: an initial denaturation at 94° C. for 5 minutes; followed by 35 cycles of PCR, one cycle being 94° C. for 20 seconds, 53° C. for 20 seconds, and 72° C. for 3 minutes; followed by 72° C. for 10 minutes.

The resulting PCR product was purified using the Qiaquick PCR Purification Kit (manufactured by Qiagen) in accordance with the instruction attached to the kit. The DNA fragment after the purification was digested with Bam HI and XhoI, since the oligonucleotide of SEQ ID NO: 4 contains a Bam HI restriction site and the oligonucleotide of SEQ ID NO: 5 contains a Xho I restriction site.

The Bam HI/XhoI DNA fragment of cotton aphid choline acetyltransferase gene was analyzed by an agarose gel electrophoresis, isolated, purified and ligated into the Bam HI/XhoI cloning sites of the $E.$ $coli$ expression vector pET41a (+) (manufactured by Novagen). The obtained vector was called pGBJ005.

Translation of the recombinant choline acetyltransferase together with two His-tags and one GST-tag provided a recombinant protein of 1021 amino acids.

Following the procedures described in Qiagen Plasmid Purification Handbook, pGBJ005 was prepared using a Qiafilter Plasmid Maxiprep (Qiagen).

Example 5

Preparation of Recombinant $E.$ $coli$

Competent cells of $E.$ $coli$ BL21 (DE3) (manufactured by Invitrogen) were transformed following the manufacturers instruction, using 1 μl of pGBJ005 at a concentration of 1 ng/μl. Colonies of the transformed $E.$ $coli$ were grown on LB agar plates containing 50 mg/L Kanamycin (manufactured by Sigma) at 37° C. overnight.

Example 6

Expression of Choline Acetyltransferase in $E.$ $coli$ $E.$ $coli$ BL21 (DE3) transformed with pGBJ005 was rotary cultured overnight in LB-medium containing 50 mg/L of Kanamycin (manufactured by Sigma) at 37° C., 250 rpm. In the next morning, the culture was diluted 1/100 in LB medium containing 50 mg/L of Kanamycin, to which IPTG was added until a final concentration of 10 μM, and grown at 22° C., 60 rpm for 4 days to produce recombinant choline acetyltransferase protein in the $E.$ $coli$. The culture was centrifuged at 7,000 rpm for 10 minutes to collect the $E.$ $coli$. The supernatant was discarded, and the remaining $E.$ $coli$ was flash frozen in liquid nitrogen and stored at −80° C. until usage.

Example 7

Purification of choline acetyltransferase

The cotton aphid choline acetyltransferase was cloned in pET41a(+) in frame with a N-terminal GST (glutathione S-transferase)-tag and His-tag and a C-terminal 6×His-tag (SEQ ID NO: 6). The recombinant choline acetyltransferase protein was purified utilizing His-tag.

(1) Preparation of Crude Extract

The frozen cell pellets of induced E. coli BL21 (DE3) cell were resuspended in 30 ml of breaking buffer (0.1M Sodium phosphate buffer pH 7.6, 1 tablet of Complete EDTA-free protease inhibitor cocktail (manufactured by Roch)), and subsequently lysed in breaking buffer by using French press (manufactured by Thermo Spectronic). The pressure was maintained at 1300 to 1500 psi during the procedure of breaking of the cells. The French pressed solution was centrifuged for 60 minutes at 14,000 rpm at 2° C. to collect a supernatant. The collected supernatant was filtered through a 0.45 µm filter and kept on ice.

(2) Purification Utilizing His-Tag

The recombinant protein was purified by utilizing metal affinity chromatography, using either the HiTrap Chelating HP (Amersham biosciences) or HisTrap HP (Amersham biosciences) columns, according to the instructions of the manufacturer (Amersham biosciences). For larger scale purifications, a XK-16/20 column (Amersham biosciences) was used, the column being filled with Chelating Fast Flow Sepharose (Amersham biosciences). The purification procedure was undertaken on the AKTA-FPLC (Amersham biosciences).

Hitrap, HisTrap, and AX-16/20 affinity columns have been prepared according to the manufacturer's protocol. Buffer A, the binding buffer, was made of 0.1M Sodium phosphate buffer pH 7.6, and 10% glycerol. Buffer B, the elution buffer, was made of 0.1M Sodium phosphate buffer pH 7.6, 500 mM imidazole, and 10% glycerol.

The purification of cotton aphid choline acetyltransferase utilizing a His-tag was performed as the following procedure:
(i) sample injection;
(ii) washing out unbound sample with 5 column volumes (CV) of 95% buffer A/5% buffer B (25 mM imidazole);
(iii) washing for 15 CV of 90% buffer A/10% buffer B (50 mM imidazole);
(iv) washing for 15 CV of 85% buffer A/15% buffer B (75 mM imidazole);
(v) washing for 15 CV of 80% buffer A/20% buffer B (100 mM imidazole);
(vi) elusion of purified protein with 15 CV of 60% buffer A/40% buffer B (200 mM imidazole); and
(vii) washing the column with 5 CV of 100% buffer B (500 mM imidazole).

The fractions obtained from the elution with 60% buffer A/40% buffer B were pooled and stored on ice.

The obtained elution fractions were analysed to verify presence of the recombinant cotton aphid choline acetyltransferase protein. An 8% polyacrylamide gel was used for optimal gel electrophoresis resolution of the expressed choline acetyltransferase protein of 115 kDa.

The following staining solution and destain solution were used for Coomassie staining of polyacrylamide gel. Staining solution was made of 1 g/l Coomassie Brilliant blue R, 50 (v/v) % Methanol, 12 (v/v) % Acetic acid and 38 (v/v) % distilled water. After mixing, the solution was filtered to get out unsoluble Brilliant blue R dye. Destain solution was made of 25 (v/v) % Methanol, 10 (v/v) % Acetic acid and 65 (v/v) % distilled water.

For western blot analysis, an anti-His (H15) sc-803 rabbit polyclonal IgG antibody (tebubio) was used as primary antibody at a 1:500 dilution. The secondary antibody was a goat anti-rabbit-HRP (Pierce) at a dilution of 1:10000.

After analysis of the polyacrylamide gels by SDS-PAGE and Western blotting, the fractions of interest were pooled and the protein concentration was determined. Protein Concentration was determined by Bradford method with the Bradford Bio-Rad protein assay (Bio-Rad) using Pre-diluted Protein Assay Standards (Pierce): Bovine Serum Albumin Fraction V Set according to the manufacturer's protocol. The pooled fractions were then distributed into several aliquots and immediately flash-frozen in liquid nitrogen and stored at −80° C.

Example 8

Selection of Compounds Inhibiting Choline Acetyltransferase Activity

Selection of a compound which modulates a choline acetyltransferase activity was performed in a system for measuring and evaluating the choline acetyltransferase activity, the activity being modulated by adding a test compound to an in vitro reaction system using the cotton aphid choline acetyltransferase prepared in Example 7.

As for a measurement of the cotton aphid choline acetyltransferase activity, after the enzymatic reaction of choline acetyltransferase using acetyl-CoA and choline as substrates, free CoA formed by choline acetyltransferase reaction was measured using 5,5'-dithio-bis(2-nitrobenzoic acid) (DTNB) reagent. DTNB reacts with free thiol groups in solution to produce 5-thio-2-nitrobenzoic acid (TNB). TNB is yellow and has absorption maximum at 412 nm. The produced TNB was measured calorimetrically to calculate choline acetyltransferase activity.

For measuring the activity, the activity of the aphid choline acetyltransferase was measured when a test compound dissolved in DMSO was contained to a final concentration of 10 µM. In addition, the activity of the aphid choline acetyltransferase was measured when DMSO was contained in place of a test compound. Then, a ratio (%) of a measured value of the activity of the aphid choline acetyltransferase when a test compound dissolved in DMSO was contained, relative to a measured value of the activity of aphid choline acetyltransferase when DMSO was contained in place of the test compound was calculated, and a value obtained by subtracting the calculated value from 100% was adopted as an inhibition degree (%). The results in each test compound are shown in Table 4 in Example 9 together with results of Example 9.

The activity of aphid choline acetyltransferase was measured when a test compound dissolved in DMSO was contained to a final concentration of each concentration of 100 µM, 30 µM, 10 µM, 3 µM, 1 µM, 0.3 µM, 0.1 µM or 0.03 µM. $IC_{50}$ (µM) was calculated from the result of each concentration at each test compound using a concentration-dependent test analyzing software XL fit (manufactured by idbs). The results are shown in Table 5 in Example 10 together with results of Example 9.

Example 9

Pesticidal Activity Test

A sterilized artificial feed having the following composition (Table 3) was prepared. Then, according to the same manner as that of the method described in Handbook of Insect Rearing Vol. 1 (Elsevier Science Publishers 1985) pp. 35 to pp. 36 except that a test compound dissolved in DMSO to a final concentration of 50 ppm was added at 0.5% volume of the artificial feed, and components were mixed, *Aphis gossypii* was reared. Six days after rearing, the number of surviving *Aphis gossypii* was investigated, and an entity exhibiting a significant controlling value (e.g. controlling value of 30% or more) was determined to have pesticidal activity by obtaining a controlling value by the following equation.

Controlling value (%) = {1−($Cb \times Tai$)/($Cai \times Tb$)} × 100

Letters in the equation represent the following meanings.
Cb: Number of surviving worms before treatment in non-treated section
Cai: Number of surviving worms at observation in non-treated section
Tb: Number of surviving worms before treatment in treated section
Tai: Number of surviving worms at observation in treated section Results are shown in Table 4 in Example 9 together with results of Example 8.

TABLE 3

| | (mg/100 ml) |
|---|---|
| Amino acid | |
| L-alanine | 100.0 |
| L-arginine | 275.0 |
| L-asparagine | 550.0 |
| L-aspartic acid | 140.0 |
| L-cysteine (hydrochloride) | 40.0 |
| L-glutamic acid | 140.0 |
| L-glutamine | 150.0 |
| L-glycine | 80.0 |
| L-histidine | 80.0 |
| L-isoleucine | 80.0 |
| L-leucine | 80.0 |
| L-lysine (hydrochloride) | 120.0 |
| L-methionine | 80.0 |
| L-phenylalanine | 40.0 |
| L-proline | 80.0 |
| L-serine | 80.0 |
| L-threonine | 140.0 |
| L-tryptophan | 80.0 |
| L-tyrosine | 40.0 |
| L-valine | 80.0 |
| Vitamins | |
| Ascorbic acid | 100.0 |
| Biotin | 0.1 |
| Calcium pantothenate | 5.0 |
| Choline chloride | 50.0 |
| Inositol | 50.0 |
| Nicotinic acid | 10.0 |
| Thiamine | 2.5 |
| Others | |
| Sucrose | 12500.0 |
| Dipotassium hydrogen phosphate | 1500.0 |
| Magnesium sulfate | 123.0 |
| Cupric chloride | 0.2 |
| Ferric chloride | 11.0 |
| Manganese chloride | 0.4 |
| Zinc sulfate (anhydrous) | 0.8 |
| Adjusted to pH 6.8 | |

TABLE 4

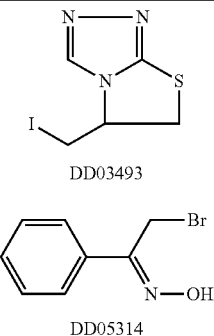

DD03493

DD05314

| Compound | Result of Example 8 Activity of inhibiting choline acetyltransferase activity (inhibition degree (%) at 10 µM addition) | Result of Example 9 Determination result of pesticidal activity |
|---|---|---|
| DD03493 | 49 | Presence of pesticidal activity |
| DD05314 | 50 | Presence of pesticidal activity |
| DF07204 | 71 | Presence of pesticidal activity |

Example 10

Pesticidal Activity Test

According to the same manner as that of Example 9, pesticidal activity test was performed, and results are shown in Table 5 in Example 10 together with results of Example 8.

TABLE 5

| Compound | Result of Example 8 Activity of inhibiting choline acetyltransferase activity (IC50, µM) | Result of Example 10 Determination result of pesticidal activity |
|---|---|---|
| 2-(α-naphthoyl)ethyl-dimethylammonium chloride (α-NEDA) | 33.5 | Presence of pesticidal activity |
| 2-(α-naphthoyl)ethyl-trimethylammonium iodide(α-NETA) | 1.5 | Presence of pesticidal activity |
| DD03493 | 23.8 | Presence of pesticidal activity |
| Cisapride | >100 | Absence of pesticidal activity |
| DL-Chlorpheniramine Maleate | >100 | Absence of pesticidal activity |

Industrial Applicability

According to the present invention, it becomes possible to provide a more target-based approach of screening agricultural chemicals, whereby compounds are screened against a specific target with intent of chemically interfering with the target site to control insects or other pest organisms.

Free Text in Sequence Listing
SEQ ID NO: 4
Designed Oligonucleotide Primer for PCR
SEQ ID NO: 5
Designed Oligonucleotide Primer for PCR

The invention claimed is:

1. A method for assaying pesticidal activity of a test substance, which comprises:
  (1) a first step of measuring the activity of a choline acetyltransferase selected from the group consisting of (a) to (h) in a reaction system in which said choline acetyltransferase contacts with a test substance; and
  (2) a second step of evaluating the pesticidal activity of said test substance based on the difference obtained by comparing the activity measured in the first step with the activity of a control:
  (a) a protein comprising the amino acid sequence of SEQ ID NO: 1;
  (b) a protein comprising an amino acid sequence that has sequence identity of at least 90% to the amino acid sequence of SEQ ID NO: 1, wherein said protein has choline acetyltransferase activity;
  (c) a protein comprising an amino acid sequence that has sequence similarity of at least 90% to the amino acid sequence of SEQ ID NO: 1, wherein said protein has choline acetyltransferase activity;
  (d) a protein comprising the amino acid sequence encoded by the nucleotide sequence of SEQ ID NO: 2 or 3;
  (e) a protein comprising an amino acid sequence encoded by a nucleotide sequence that has sequence identity of at least 90% to the nucleotide sequence of SEQ ID NO: 2 or 3, wherein said protein has choline acetyltransferase activity;
  (f) a protein comprising an amino acid sequence encoded by a polynucleotide, wherein said polynucleotide hybridizes under stringency conditions comprising a salt concentration of about 6.0×SSC and a temperature of about 65° C., to a polynucleotide comprising a nucleotide sequence complementary to the nucleotide sequence of SEQ ID NO: 2 or 3, and wherein said protein has choline acetyltransferase activity;
  (g) a protein comprising an amino acid sequence of an insect choline acetyltransferase; and
  (h) a protein comprising an amino acid sequence of a cotton aphid choline acetyltransferase.

2. A method for screening a pesticidal substance, which comprises selecting a substance having the pesticidal activity that is evaluated by the method of claim 1.

3. The method of claim 1, wherein the choline acetyltransferase is a protein comprising the amino acid sequence of SEQ ID NO: 1.

4. The method of claim 1, wherein the choline acetyltransferase is a protein comprising an amino acid sequence that has sequence identity of at least 90% to the amino acid sequence of SEQ ID NO: 1, wherein said protein has choline acetyltransferase activity.

5. The method of claim 1, wherein the choline acetyltransferase is a protein comprising an amino acid sequence that has sequence similarity of at least 90% to the amino acid sequence of SEQ ID NO: 1, wherein said protein has choline acetyltransferase activity.

6. The method of claim 1, wherein the choline acetyltransferase is a protein comprising the amino acid sequence encoded by the nucleotide sequence of SEQ ID NO: 2 or 3.

7. The method of claim 1, wherein the choline acetyltransferase is a protein comprising an amino acid sequence encoded by a nucleotide sequence that has sequence identity of at least 90% to the nucleotide sequence of SEQ ID NO: 2 or 3, wherein said protein has choline acetyltransferase activity.

8. The method of claim 1, wherein the choline acetyltransferase is an insect choline acetyltransferase.

9. The method of claim 1, wherein the choline acetyltransferase is a cotton aphid choline acetyltransferase.

* * * * *

UNITED STATES PATENT AND TRADEMARK OFFICE
CERTIFICATE OF CORRECTION

| | | |
|---|---|---|
| PATENT NO. | : 8,476,035 B2 | Page 1 of 1 |
| APPLICATION NO. | : 12/743866 | |
| DATED | : July 2, 2013 | |
| INVENTOR(S) | : Junko Otsuki et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 360 days.

Signed and Sealed this
Seventeenth Day of June, 2014

Michelle K. Lee
*Deputy Director of the United States Patent and Trademark Office*

SEQUENCE LISTING

<160> NUMBER OF SEQ ID NOS: 6

<210> SEQ ID NO 1
<211> LENGTH: 736
<212> TYPE: PRT
<213> ORGANISM: Aphis gossypii

<400> SEQUENCE: 1

```
Val Lys Val Asp Thr Asp Ala Ala His Ala Thr Ala Asp Gln Val Gly
1               5                   10                  15

Pro Ala Ala Gly Asp Gly Gly Thr Gly Gly Lys Leu His Ala
            20                  25                  30

Ala Ile Val Ala Ser Val Ala Ala Ser Pro Gln Lys Leu Ala Thr Thr
            35                  40                  45

Ile Arg Gly Phe Trp Asn Ser Ser Ala Gly Pro Ala Ala Asn Ser Val
        50                  55                  60

Leu Gly Trp Arg Gly Asn Ile Lys Glu Thr Ile Ala Lys Gly Trp Trp
65                  70                  75                  80

Asn Leu Asn Thr Glu Arg Ser Asp Lys Glu Val Val Ala Asp Ser Gly
                85                  90                  95

Glu Gln Arg Pro Arg Thr Pro Asp Glu Thr Lys Leu Pro Lys Leu
            100                 105                 110

Pro Val Pro Leu Leu Glu Arg Thr Thr Lys Leu Tyr Leu Glu Thr Leu
            115                 120                 125

Lys Pro Ile Leu Asn Glu Lys Gln Tyr Glu His Ala Lys Lys Leu Val
    130                 135                 140

Ala Asp Phe Thr Ser Gly Pro Gly Pro Met Leu Gln Glu Ile Leu Ile
145                 150                 155                 160

Glu Arg Arg Glu Glu His Asp Asn Trp Val Tyr Asp Trp Leu His
                165                 170                 175

Asp Met Tyr Leu Cys Asn Gln Leu Pro Leu Pro Val Asn Ser Asn Pro
            180                 185                 190

Gly Met Val Phe Pro Pro Leu Pro Asn Leu Ser Ala Glu Thr Arg Met
            195                 200                 205

Ala Lys Phe Ser Ala Arg Phe Val Val Glu Met Met Asn Phe Lys Arg
    210                 215                 220

Ile Leu Asp Lys Arg Glu Leu Pro Val Glu Lys Ala Ala Ser Arg Glu
225                 230                 235                 240

Lys Gly Gln Pro Leu Cys Met Ala Gln Tyr Tyr Arg Leu Met Lys Ser
                245                 250                 255

Tyr Arg Glu Pro Gly Leu Val Lys Asp Arg Leu Val Asn Phe Glu Ser
            260                 265                 270

Asp Leu Thr Leu Ser Arg Pro His Ile Ile Val Ala Cys Lys Ser Gln
            275                 280                 285

Phe Tyr Val Leu Arg Leu Thr Ser Gly Glu Asp Ala Thr Pro Ile Thr
    290                 295                 300

Glu Glu Glu Ile Val Thr Lys Leu Leu Asn Ile Ile Met Asp Ala Lys
305                 310                 315                 320

Lys Ser Ala Gly Thr Ala Gly Ser Tyr Ser Val Gly Ile Leu Thr Ser
                325                 330                 335

Gln Lys Arg Asp Asp Trp Ala His Ser Arg Glu Leu Leu Met Lys Ser
            340                 345                 350

Ala Ser Asn Arg Asn Asn Leu Ala Leu Ile Glu Arg Cys Leu Phe Phe
            355                 360                 365
```

Ile Asn Phe Asp Leu Glu Pro Leu Gly Leu Glu Phe Asn Ser Thr Cys
370                 375                 380

Lys Val Gly Ala Lys Gly Tyr Arg Leu Ser Asn Asp Arg Asp Glu Thr
385                 390                 395                 400

Asn Met Met His Gln Met Ile His Gly Gly Ser Glu Tyr Cys Ser
            405                 410                 415

Gly Asn Arg Trp Phe Asp Lys Thr Ile Gln Leu Ile Gly Arg Asp
        420                 425                 430

Gly Ala Asn Gly Leu Cys Tyr Glu His Ser Pro Ala Glu Gly Ile Ala
        435                 440                 445

Val Ile Glu Leu Met Glu Lys Leu Ile Lys Ser Thr Lys Asp Leu Asn
450                 455                 460

Glu Gln Pro Ile Asp Ile Ile Thr Ser Thr Glu Lys Pro Glu Lys Leu
465                 470                 475                 480

Ile Trp Ser Val Asn Asn Glu Leu Ile Lys His Ile Ala Asp Ala Ser
            485                 490                 495

Thr Val Leu Asp Lys Leu Val Lys Asp Leu Asn Phe His Val Phe Arg
            500                 505                 510

Phe Thr Gln Tyr Gly Lys Glu Phe Ile Lys Ser Cys Lys Ile Ser Pro
        515                 520                 525

Asp Val Tyr Ile Gln Leu Ala Met Gln Leu Ala Tyr His Lys Leu His
530                 535                 540

Gly Lys Leu Val Ala Thr Tyr Glu Ser Ala Ser Thr Arg Arg Phe Arg
545                 550                 555                 560

Leu Gly Arg Val Asp Cys Ile Arg Ala Ala Thr Val Glu Ala Leu Glu
            565                 570                 575

Trp Ala Lys Ala Met Asn Gln Ser Ala Val Thr Glu Thr Gly Ile Leu
            580                 585                 590

Gly Thr Lys Lys Ile Tyr Tyr Thr Val Thr Asp Asn Glu Lys Leu Gln
            595                 600                 605

Leu Phe Glu Thr Ala Val Lys Lys Gln Thr Asp Ile Met Ile Asp Asn
610                 615                 620

Ile Leu Gly Met Gly Ile Asp Thr His Leu Leu Gly Leu Arg Gln Ala
625                 630                 635                 640

Ala Arg Glu Asn Ala Ile Ser Cys Ala Val Phe Glu Asp Asp Ser Phe
            645                 650                 655

Arg Ile Ala Asn His Phe Ala Leu Ser Thr Ser Gln Leu Leu Thr Ser
            660                 665                 670

Thr Asp Ser Phe Met Gly Tyr Gly Pro Val Val Pro Asp Gly Tyr Gly
        675                 680                 685

Val Ser Tyr Asn Pro Gln Ser Asn Thr Leu Val Phe Cys Val Ser Ser
        690                 695                 700

Phe Lys Ser Ser Lys Thr Thr Asn Asn Asn Ala Phe Thr Val Ala Leu
705                 710                 715                 720

Glu Gln Ser Leu Met Ala Met Gln Lys Leu Ile Tyr Met Lys Arg Asn
            725                 730                 735

<210> SEQ ID NO 2
<211> LENGTH: 2211
<212> TYPE: DNA
<213> ORGANISM: Aphis gossypii

<400> SEQUENCE: 2
gtcaaggtgg atacggacgc ggcgcacgcg acggccgacc aggtcggacc ggctgcggcg    60

| | |
|---|---|
| ggagacggcg gcacgaccgg cggcaaactg cacgcggcga tcgtagcgtc cgtggcggcg | 120 |
| tcgccgcaga agttggccac caccatcaga ggcttctgga actcgtccgc gggcccggct | 180 |
| gccaattcgg ttctgggatg gcgggaaat atcaaggaaa cgatcgcaaa agggtggtgg | 240 |
| aatctaaata cggaacgatc ggacaaggag gtggttgcag actcgggcga caacgacca | 300 |
| agaacaccgg acgaagagac aaaactacca aaactaccag tgcctttgtt ggaacgtact | 360 |
| acgaaattat atctgaaaac gctgaaacca atactgaacg agaaacaata cgaacacgct | 420 |
| aaaaagctag tggcagattt cacgagtggt cctggtccaa tgctacaaga aatattgatt | 480 |
| gaacgcagag aagaacatga caattgggtg tatgattggt ggcttcacga catgtatctc | 540 |
| tgcaaccaat taccattgcc agttaattcc aatcccggaa tggtattcc acctcttcca | 600 |
| aatctttctg cagaaacacg aatggccaaa ttttcagcta gatttgtagt tgaaatgatg | 660 |
| aatttcaaac gtatattgga caagcgagaa cttcccgtag aaaaagctgc atctagagaa | 720 |
| aagggacaac cgttatgcat ggcacaatat tatagactaa tgaaatcata tagggaacca | 780 |
| ggattagtta aggatcgact cgtaaacttc gaatcagatt tgacattatc gaggcctcat | 840 |
| attattgttg catgcaagtc acagttttat gtgttgcgat tgcatcgggc gaagacgca | 900 |
| actcccataa cggaagaaga aattgtcaca aaactactga acatcataat ggacgcaaaa | 960 |
| aaatcggctg gcaccgcggg ttcatattct gtgggcattt taacatcaca aaaagagat | 1020 |
| gactgggcgc atagcagaga gttattgatg aagagtgctt ctaaccgcaa taattggcg | 1080 |
| ttaattgagc gttgcttgtt tttcatcaat tttgatttgg aaccacttgg tctagaattt | 1140 |
| aattctacat gcaaagtagg tgcaaaaggt tatagactat caaatgacag agacgagaca | 1200 |
| aatatgatgc atcaaatgat ccatggtgga ggtagtgagt actgttctgg taaccgctgg | 1260 |
| tttgacaaga ctatacaatt gataattggg agagatggtg cgaatggatt atgttacgag | 1320 |
| cattcaccgg cggaaggaat cgcagttatt gaattaatgg aaaaattgat taaaagtacc | 1380 |
| aaagacttga cgaacaacc aatagatata ataacatcga cagaaaaacc agaaaaactc | 1440 |
| atatggagtg ttaataatga actcatcaaa cacatagctg atgcttctac tgtcttggat | 1500 |
| aagttagtca aagatttgaa cttccatgtg ttccgattca ctcaatacgg aaaagaattc | 1560 |
| ataaagtctt gtaagatcag tccagatgtt tacatacaac ttgcgatgca attagcttat | 1620 |
| cataagcttc acggcaaact ggtagctaca tacgagagcg cctccaccag acgtttccga | 1680 |
| ttgggtagag tggattgtat acgggcggcg acggtggaag cactggaatg ggccaaagca | 1740 |
| atgaatcagt cggccgtcac cgagactggc atattaggca caagaagat atactacaca | 1800 |
| gtgactgata acgaaaaact tcaacttttc gaaactgcag tgaaaaaaca aactgacatt | 1860 |
| atgatagaca atattctcgg aatgggaata gatactcact tattgggatt gagacaagca | 1920 |
| gcaagagaaa atgccatatc gtgtgcagta tttgaagacg attcgtttag aattgccaat | 1980 |
| cattttgcgt tatcaacaag tcaactatta acttccacgg acagttttat gggctatgga | 2040 |
| ccagttgtac ccgacggcta tggcgtttcc tataatcccc aaagtaacac tttggtattc | 2100 |
| tgtgtatctt cgttcaaatc atctaaaacc acaaacaaca atgcttttac ggttgctcta | 2160 |
| gaacaaagtt tgatggcaat gcagaaattg atatacatga aagaaatta a | 2211 |

<210> SEQ ID NO 3
<211> LENGTH: 2360
<212> TYPE: DNA
<213> ORGANISM: Aphis gossypii

<400> SEQUENCE: 3

```
gattgcacac gggggagtcg cggcgtggcc ttgacgctcg gtcaaggtgg atacggacgc    60
ggcgcacgcg acggccgacc aggtcggacc ggctgcggcg ggagacggcg gcacgaccgg   120
cggcaaactg cacgcggcga tcgtagcgtc cgtggcggcg tcgccgcaga agttggccac   180
caccatcagg ggcttctgga actcgtccgc gggcccggct gccaattcgg ttctgggatg   240
gcggggaaat atcaaggaaa cgatcgcaaa agggtggtgg aatctaaata cggaacgatc   300
ggacaaggag gtgttgcag actcgggcga caacgacca agaacaccgg acgaagagac    360
aaaactacca aaactaccag tgcctttgtt ggaacgtact acgaaattat atctggaaac   420
gctgaaacca atactgaacg agaaacaata cgaacacgct aaaaagctag tggcagattt   480
cacgagtggt cctggtccaa tgctacaaga aatattgatt gaacgcagag aagaacatga   540
caattgggtg tatgattggt ggcttcacga catgtatctc tgcaaccaat taccattgcc   600
agttaattcc aatcccggaa tggtatttcc acctcttcca aatctttctg cagaaacacg   660
aatggccaaa ttttcagcta gatttgtagt tgaaatgatg aatttcaaac gtatattgga   720
caagcgagaa cttcccgtag aaaaagctgc atctagagaa aagggacaac cgttatgcat   780
ggcacaatat tatagactaa tgaaatcata tagggaacca ggattagtta aggatcgact   840
cgtaaacttc gaatcagatt tgacattatc gaggcctcat attattgttg catgcaagtc   900
acagttttat gtgttgcgat tgacatcggg cgaagacgca actcccataa cggaagaaga   960
aattgtcaca aaactactga acatcataat ggacgcaaaa aaatcggctg gcaccgcggg  1020
ttcatattct gtgggcattt taacatcaca aaaaagagat gactgggcgc atagcagaga  1080
gttattgatg aagagtgctt ctaaccgcaa taatttggcg ttaattgagc gttgcttgtt  1140
tttcatcaat tttgatttgg aaccacttgg tctagaattt aattctacat gcaaagtagg  1200
tgcaaaaggt tatagactat caaatgacag agacgagaca aatatgatgc atcaaatgat  1260
ccatggtgga ggtagtgagt actgttctgg taaccgctgg tttgacaaga ctatacaatt  1320
gataattggg agagatggtg cgaatggatt atgttacgag cattcaccgg cggaaggaat  1380
cgcagttatt gaattaatgg aaaaattgat taaaagtacc aaagacttga acgaacaacc  1440
aatagatata ataacatcga cagaaaaacc agaaaaactc atatggagtg ttaataatga  1500
actcatcaaa cacatagctg atgcttctac tgtcttggat aagttagtca aagatttgaa  1560
cttccatgtg ttccgattca ctcaatacgg aaaagaattc ataaagtctt gtaagatcag  1620
tccagatgtt tacatacaac ttgcgatgca attagcttat cataagcttc acggcaaact  1680
ggtagctaca tacgagagcg cctccaccag acgtttccga ttgggtagag tggattgtat  1740
acgggcggcg acggtggaag cactggaatg ggccaaagca atgaatcagt cggccgtcac  1800
cgagactggc atattaggca caaagaagat atactacaca gtgactgata acgaaaaact  1860
tcaacttttc gaaactgcag tgaaaaaaca aactgacatt atgatagaca atattctcgg  1920
aatgggaata gatactcact tattgggatt gagacaagca gcaagagaaa atgccatatc  1980
gtgtgcagta tttgaagacg attcgtttag aattgccaat cattttgcgt tatcaacaag  2040
tcaactatta acttccacgg acagtttttat gggctatgga ccagttgtac ccgacggcta  2100
tggcgttttcc tataatcccc aaagtaacac tttggtattc tgtgtatctt cgttcaaatc  2160
atctaaaacc acaaacaaca atgctttttac ggttgctcta gaacaaagtt tgatggcaat  2220
gcagaaattg atatacatga aaagaaatta agacaacgtt gtttataatg tttgcatacg  2280
tttttgcgat ttatatctca tcatatcatt agtaccataa acatatcatt gagtgattaa  2340
ataatttaa tattgtattc                                               2360
```

```
<210> SEQ ID NO 4
<211> LENGTH: 32
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 4
ggatccgtca aggtggatac ggacgcggcg ca                                    32

<210> SEQ ID NO 5
<211> LENGTH: 42
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 5
ctcgagttaa tttcttttca tgtatatcaa tttctgcatt gc                         42

<210> SEQ ID NO 6
<211> LENGTH: 6
<212> TYPE: PRT
<213> ORGANISM: Artificial Sequence
<220> FEATURE:
<223> OTHER INFORMATION: Description of Artificial Sequence: Synthetic
      6xHis tag

<400> SEQUENCE: 6

His His His His His His
1               5
```